United States Patent
Jiang et al.

(10) Patent No.: US 11,278,550 B2
(45) Date of Patent: Mar. 22, 2022

(54) COMPOSITIONS AND METHODS FOR THE TREATMENT OF PRADER-WILLI SYNDROME

(71) Applicants: Duke University, Durham, NC (US); The University of North Carolina at Chapel Hill, Chapel Hill, NC (US)

(72) Inventors: Yong-hui Jiang, Durham, NC (US); Yuna Kim, Durham, NC (US); Hyeong-min Lee, Chapel Hill, NC (US); Jian Jin, New York, NY (US); Bryan L. Roth, Durham, NC (US)

(73) Assignees: Duke University, Durham, NC (US); The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 16/301,511

(22) PCT Filed: May 17, 2017

(86) PCT No.: PCT/US2017/033171
§ 371 (c)(1),
(2) Date: Nov. 14, 2018

(87) PCT Pub. No.: WO2017/201199
PCT Pub. Date: Nov. 23, 2017

(65) Prior Publication Data
US 2019/0201402 A1 Jul. 4, 2019

Related U.S. Application Data

(60) Provisional application No. 62/337,637, filed on May 17, 2016.

(51) Int. Cl.
*A61K 31/517* (2006.01)
*C07D 401/14* (2006.01)
(Continued)

(52) U.S. Cl.
CPC .......... *A61K 31/517* (2013.01); *A61K 31/551* (2013.01); *A61P 43/00* (2018.01); *C07D 401/02* (2013.01); *C07D 401/14* (2013.01)

(58) Field of Classification Search
CPC ................................................... A61K 31/517
(Continued)

(56) References Cited

U.S. PATENT DOCUMENTS

2013/0317018 A1 11/2013 Philpot
2015/0274660 A1 10/2015 Pliushchev et al.

FOREIGN PATENT DOCUMENTS

WO  WO 00/00823  1/2000
WO  WO 00/39585  7/2000
(Continued)

OTHER PUBLICATIONS

Cassidy & Driscoll. "Prader-Willi syndrome," Eur. J. Hum. Genet. 17, 3-13 (2009).
(Continued)

*Primary Examiner* — Shengjun Wang
(74) *Attorney, Agent, or Firm* — Polsinelli PC

(57) ABSTRACT

The invention provides pharmaceutical compositions and methods of use thereof for treating Prader-Willi syndrome. More specifically, the invention provides pharmaceutical compositions that when administered inhibit the G9a driven methylation of histone H3 lysine 9.

16 Claims, 21 Drawing Sheets

Specification includes a Sequence Listing.

(51) Int. Cl.
  *C07D 401/02* (2006.01)
  *A61P 43/00* (2006.01)
  *A61K 31/551* (2006.01)
(58) Field of Classification Search
  USPC .................................................. 514/266.22
  See application file for complete search history.

(56) References Cited

FOREIGN PATENT DOCUMENTS

| WO | 2015/192981 A1 | 12/2015 |
| WO | WO 2017/181177 A1 | 10/2017 |
| WO | 2018/183923 A1 | 10/2018 |

OTHER PUBLICATIONS

Buiting, K. "Prader-Willi Syndrome and Angelman Syndrome," Am J Med Genet C Semin Med Genet. 154C, 365-376 (2010).
Buiting, K., et al., "Clinical phenotypes of MAGEL2 mutations and deletions," Orphanet J. Rare Dis. 9, 40 (2014).
Schaaf, C.P., et al., "Truncating mutations of MAGEL2 cause Prader-Willi phenotypes and autism," Nat. Genet. 45, 1405-1408 (2013).
Kanber, D., et al., "A paternal deletion of MKRN3, MAGEL2 and NDN does not result in Prader-Willi syndrome," Eur J Hum Genet 17, 582-590 (2009).
Sahoo, T., et al., "Prader-Willi phenotype caused by paternal deficiency for the HBII-85 C/D box small nucleolar RNA cluster," Nat Genet. 40, 719-721 (2008).
de Smith, A.J., et al., "A deletion of the HBII-85 class of small nucleolar RNAs (snoRNAs) is associated with hyperphagia, obesity and hypogonadism," Hum Mol Genet. 18, 3257-3265 (2009).
Duker, A.L., et al., "Paternally inherited microdeletion at 15q11.2 confirms a significant role for the SNORD116 C/D box snoRNA cluster in Prader-Willi syndrome," Eur J Hum Genet. 18, 1196-1201 (2010).
Bieth, E., et al., "Highly restricted deletion of the SNORD116 region is implicated in Prader-Willi Syndrome," Eur J Hum Genet.: EJHG 23, 252-255 (2015).
Runte, M., et al., "Prader-Willi phenotype caused by paternal deficiency for the HBII-85 C/D box small nucleolar RNA cluster," Hum. Mol. Genet. 10, 2687-2700 (2001).
de los Santos, et al., "Small Evolutionarily Conserved RNA, Resembling C/D Box Small Nucleolar RNA, Is Transcribed from PWCR1, a Novel Imprinted Gene in the Prader-Willi Deletion Region, Which Is Highly Expressed in Brain," Am. J. Hum. Genet. 67, 1067-1082 (2000).
Gallagher, et al., "Evidence for the Role of PWCR1/HBII-85 C/D Box Small Nucleolar RNAs in Prader-Willi Syndrome," Am. J. Hum. Genet. 71, 669-678 (2002).
Saitoh, S., et al., "Minimal definition of the imprinting center and fixation of chromosome 15q11-q13 epigenotype by imprinting mutations.," Proc Natl Acad Sci U S A, 93, 7811-7815 (1996).
Fulmer-Smentek & Francke, "Association of acetylated histones with paternally expressed genes in the Prader-Willi deletion region.," Hum. Mol. Genet. 10, 645-652 (2001).
Saitoh & Wada, "Parent-of-Origin Specific Histone Acetylation and Reactivation of a Key Imprinted Gene Locus in Prader-Willi Syndrome," Am J Hum Genet. 66, 1958-1962 (2000).
Huang, H.S., et al.,"Topoisomerase inhibitors unsilence the dormant allele of Ube3a in neurons," Nature 481, 185-189 (2012).
Vedadi, M., et al., "A chemical probe selectively inhibits G9a and GLP methyltransferase activity in cells," Nat. Chem. Biol. 7, 566-574 (2011).
Liu, F. et al., "Discovery of an in Vivo Chemical Probe of the Lysine Methyltransferases G9a and GLP," J. Med. Chem. 56, 8931-8942 (2013).
Liu, F. et al., "Optimization of Cellular Activity of G9a Inhibitors 7-Aminoalkoxy-quinazolines," J. Med. Chem. 54, 5139-6150 (2011).
Liu, F. et al., "Discovery of a 2,4-Diamino-7-aminoalkoxyquinazoline as a Potent and Selective Inhibitor of Histone Lysine Methyltransferase G9," J. Med Chem. 52, 7950-7953 (2009).
Liu, F. et al., "Protein Lysine Methyltransferase G9a Inhibitors: Design, Synthesis, and Structure Activity Relationships of 2,4 Diamino-7-aminoalkoxy-quinazolines.," J Med Chem 53, 5844-5857 (2010).
Pai, et al., "A histone H3K36 chromatin switch coordinates DNA doublestrand break repair pathway choice," Nature communications 5, 4091 (2014).
International Search Report and Written Opinion for PCT/US2017/033171, dated Aug. 25, 2017.
Xin, et al., Role of Histone Methyltransferase G9a in CpG Methylation of the Prader-Willi Syndrome Imprinting Center, Apr. 25, 2003, The Journal of Biological Chemistry, vol. 278, No. 17, pp. 14996-15000.
Kubicek, S., et al., "Reversal of H3K9me2 by a Small-Molecule Inhibitor for the G9a Histone Methylstrasferase" Mol. Cell, 2007, 25, 473-481.
Pappano, W. N. et al., The Histone Methyltransferase Inhibitor A-366 Uncovers a Role for G9a/GLP in the Epigenetics.
Sigma-Aldrich Certificate of Analysis for A-366, Sigma Product Ref. SML1410, QR Release Date Sep. 25, 2015.
Sigma-Aldrich Certificate of Analysis for BIX-01294, Sigma Product Ref. B9311, QR Release Date Jul. 15, 2009.
Sigma-Aldrich Certificate of Analysis for UNC0638, Sigma Product Ref. U4885, QR Release Date Sep. 27, 2010.
Sigma-Aldrich Certificate of Analysis for UNC0642, Sigma Product Ref. SML1037, QR Release Date May 14, 2014.
Srimongkolpithak, N. et al., "Identification of 2,4-diamino-6,7-dimethoxyquinoline derivatives as G9a inhibitors," Med. Chem. Commun., 2014, 5, 1821.
Sweis, R. F. et al., "Discovery and Development of Potent and Selective Inhibitors of Histone Methyltransferase G9a," ACS Med. Chem. Lett. 2014, 5(2), 205-209.
Dubose AJ, et al., Temporal and developmental requirements for the Prader-Willi imprinting center. PNAS. 109(9): 3446-3450 (2012).
Kim Y, et al., Targeting the histone methyltransferase G9a activates imprinted genes and improves survival of a mouse model of Prader-Willi syndrome, Nat Med., 23(2): 213-222 (2017).
Li E, et al., Targeted mutation of the DNA methyltransferase gene results in embryonic lethality, Cell, 69(6): 915-926 (1992).
San José-Enériz E, et al., Discovery of first-in-class reversible dual small molecule inhibitors against G9a and DNMTs in hematological malignancies. Nat Commun. 8:15424 (2017).
Tachibana M, et al., G9a histone methyltransferase plays a dominant role in euchromatic histone H3 lysine 9 methylation and is essential for early embryogenesis, Genes Dev., 16(14): 1779-1791 (2002).
Zoghbi HY, et al., Epigenetics and human disease, Cold Spring Harb. Perspect. Biol., 8(2): a019497 (2016).

c

UNC0638

UNC0642

UNC617

UNC618 a b c d

SEQUENCE LISTING

```
<160> NUMBER OF SEQ ID NOS: 52

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
gctgcagcac attgactata gaat                                                 24

<210> SEQ ID NO 2
<211> LENGTH: 24
<212> TYPE: DNA
<213> ORGANISM: Artificial Sequence
<220> FEATURE:
<223> OTHER INFORMATION: Primer

<400> SEQUENCE: 2
cacagtcatg gataccaagt tctc                                                 24

<210> SEQ ID NO 3
<211> LENGTH: 18
<212> TYPE: DNA
<213> ORGANISM: Artificial Sequence
<220> FEATURE:
<223> OTHER INFORMATION: Primer

<400> SEQUENCE: 3
tggatcgatg atgagtcc                                                        18

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
tggacctcag ttccgatgag a                                                    21

<210> SEQ ID NO 5
<211> LENGTH: 18
<212> TYPE: DNA
<213> ORGANISM: Artificial Sequence
<220> FEATURE:
<223> OTHER INFORMATION: Primer

<400> SEQUENCE: 5
ctggtggatc ccacaggt                                                        18

<210> SEQ ID NO 6
<211> LENGTH: 18
```

```
<212> TYPE: DNA
<213> ORGANISM: Artificial Sequence
<220> FEATURE:
<223> OTHER INFORMATION: Primer

<400> SEQUENCE: 6
agaagcccac gccacata                                                    18

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
cttcctcaca ccctggtctc                                                  20

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
gacttcaaga aatgcgtgct c                                                21

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
ggggtgggtc attatagtat tcag                                             24

<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
acaaaaatcc aagaaaggta gcac                                             24

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
ctaagaagct catcaccgaa g                                                21

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
```
ggcagatacg aaaccaagtt g                                              21

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
agagctacga gctgcctgac                                                20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
agcactgtgt tggcgtacag                                                20

<210> SEQ ID NO 15
<211> LENGTH: 22
<212> TYPE: DNA
<213> ORGANISM: Artificial Sequence
<220> FEATURE:
<223> OTHER INFORMATION: Primer

<400> SEQUENCE: 15
ttggttctga ggagtgattt gc                                             22

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
ccttgaattc caccaccttg                                                20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
ggatctatga tgattcccag                                                20

<210> SEQ ID NO 18
<211> LENGTH: 18
<212> TYPE: DNA
<213> ORGANISM: Artificial Sequence
<220> FEATURE:
<223> OTHER INFORMATION: Primer

<400> SEQUENCE: 18
ggacctcagt tccgatga                                                  18

<210> SEQ ID NO 19
<211> LENGTH: 23
<212> TYPE: DNA
<213> ORGANISM: Artificial Sequence

```
<220> FEATURE:
<223> OTHER INFORMATION: Primer

<400> SEQUENCE: 19
ggttgcattc cctttccagt atg                                            23

<210> SEQ ID NO 20
<211> LENGTH: 23
<212> TYPE: DNA
<213> ORGANISM: Artificial Sequence
<220> FEATURE:
<223> OTHER INFORMATION: Primer

<400> SEQUENCE: 20
cagcaattcc catgttcctt acc                                            23

<210> SEQ ID NO 21
<211> LENGTH: 23
<212> TYPE: DNA
<213> ORGANISM: Artificial Sequence
<220> FEATURE:
<223> OTHER INFORMATION: Primer

<400> SEQUENCE: 21
acagaacaat aggtcaccag gtt                                            23

<210> SEQ ID NO 22
<211> LENGTH: 21
<212> TYPE: DNA
<213> ORGANISM: Artificial Sequence
<220> FEATURE:
<223> OTHER INFORMATION: Primer

<400> SEQUENCE: 22
aagcaagact gttcacctca t                                              21

<210> SEQ ID NO 23
<211> LENGTH: 21
<212> TYPE: DNA
<213> ORGANISM: Artificial Sequence
<220> FEATURE:
<223> OTHER INFORMATION: Primer

<400> SEQUENCE: 23
acatgaagca gcacgacttc t                                              21

<210> SEQ ID NO 24
<211> LENGTH: 24
<212> TYPE: DNA
<213> ORGANISM: Artificial Sequence
<220> FEATURE:
<223> OTHER INFORMATION: Primer

<400> SEQUENCE: 24
gacgttgtgg ctgttgtagt tgta                                           24

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
ggcaaattca acggcacagt                                                20
```

```
<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
gggtctcgct cctggaagat                                              20

<210> SEQ ID NO 27
<211> LENGTH: 28
<212> TYPE: DNA
<213> ORGANISM: Artificial Sequence
<220> FEATURE:
<223> OTHER INFORMATION: Primer

<400> SEQUENCE: 27
ggtggttttt tttaagagat agtttggg                                     28

<210> SEQ ID NO 28
<211> LENGTH: 25
<212> TYPE: DNA
<213> ORGANISM: Artificial Sequence
<220> FEATURE:
<223> OTHER INFORMATION: Primer

<400> SEQUENCE: 28
catcccccta atccactacc ataac                                        25

<210> SEQ ID NO 29
<211> LENGTH: 29
<212> TYPE: DNA
<213> ORGANISM: Artificial Sequence
<220> FEATURE:
<223> OTHER INFORMATION: Primer

<400> SEQUENCE: 29
tatgtaatat gatatagttt agaaattag                                    29

<210> SEQ ID NO 30
<211> LENGTH: 29
<212> TYPE: DNA
<213> ORGANISM: Artificial Sequence
<220> FEATURE:
<223> OTHER INFORMATION: Primer

<400> SEQUENCE: 30
aataaaccca aatctaaaat attttaatc                                    29

<210> SEQ ID NO 31
<211> LENGTH: 28
<212> TYPE: DNA
<213> ORGANISM: Artificial Sequence
<220> FEATURE:
<223> OTHER INFORMATION: Primer

<400> SEQUENCE: 31
aatttgtgtg atgtttgtaa ttatttgg                                     28

<210> SEQ ID NO 32
<211> LENGTH: 28
<212> TYPE: DNA
<213> ORGANISM: Artificial Sequence
<220> FEATURE:
<223> OTHER INFORMATION: Primer
```

```
<400> SEQUENCE: 32
ataaaataca ctttcactac taaaatcc                                          28

<210> SEQ ID NO 33
<211> LENGTH: 22
<212> TYPE: DNA
<213> ORGANISM: Artificial Sequence
<220> FEATURE:
<223> OTHER INFORMATION: Primer

<400> SEQUENCE: 33
gcctcaggat ccccgtccca at                                                22

<210> SEQ ID NO 34
<211> LENGTH: 22
<212> TYPE: DNA
<213> ORGANISM: Artificial Sequence
<220> FEATURE:
<223> OTHER INFORMATION: Primer

<400> SEQUENCE: 34
tggaaccgga ttctgcccgg at                                                22

<210> SEQ ID NO 35
<211> LENGTH: 25
<212> TYPE: DNA
<213> ORGANISM: Artificial Sequence
<220> FEATURE:
<223> OTHER INFORMATION: Primer

<400> SEQUENCE: 35
gtctctttct tgtttttaag ctggg                                             25

<210> SEQ ID NO 36
<211> LENGTH: 21
<212> TYPE: DNA
<213> ORGANISM: Artificial Sequence
<220> FEATURE:
<223> OTHER INFORMATION: Primer

<400> SEQUENCE: 36
tgagctcatt gagacatttg g                                                 21

<210> SEQ ID NO 37
<211> LENGTH: 22
<212> TYPE: DNA
<213> ORGANISM: Artificial Sequence
<220> FEATURE:
<223> OTHER INFORMATION: Primer

<400> SEQUENCE: 37
taaccctgtt ttccaggtat gg                                                22

<210> SEQ ID NO 38
<211> LENGTH: 22
<212> TYPE: DNA
<213> ORGANISM: Artificial Sequence
<220> FEATURE:
<223> OTHER INFORMATION: Primer

<400> SEQUENCE: 38
aagctgctga tgagaagaaa cc                                                22

<210> SEQ ID NO 39
```

<211> LENGTH: 24
<212> TYPE: DNA
<213> ORGANISM: Artificial Sequence
<220> FEATURE:
<223> OTHER INFORMATION: Primer

<400> SEQUENCE: 39
ctagaggccc cctctcattg caac                                           24

<210> SEQ ID NO 40
<211> LENGTH: 24
<212> TYPE: DNA
<213> ORGANISM: Artificial Sequence
<220> FEATURE:
<223> OTHER INFORMATION: Primer

<400> SEQUENCE: 40
cttcgcacac atccccgcct gagc                                           24

<210> SEQ ID NO 41
<211> LENGTH: 22
<212> TYPE: DNA
<213> ORGANISM: Artificial Sequence
<220> FEATURE:
<223> OTHER INFORMATION: Primer

<400> SEQUENCE: 41
tcttcaaatg tgcttggatc ga                                             22

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42
gcaacgtgct ggacctcagt                                                20

<210> SEQ ID NO 43
<211> LENGTH: 22
<212> TYPE: DNA
<213> ORGANISM: Artificial Sequence
<220> FEATURE:
<223> OTHER INFORMATION: Primer

<400> SEQUENCE: 43
caatggacca agagcattga ta                                             22

<210> SEQ ID NO 44
<211> LENGTH: 22
<212> TYPE: DNA
<213> ORGANISM: Artificial Sequence
<220> FEATURE:
<223> OTHER INFORMATION: Primer

<400> SEQUENCE: 44
atagggtatt gaaaccccga gt                                             22

<210> SEQ ID NO 45
<211> LENGTH: 22
<212> TYPE: DNA
<213> ORGANISM: Artificial Sequence
<220> FEATURE:
<223> OTHER INFORMATION: Primer

<400> SEQUENCE: 45
tgagtcccac aaggaagttt tt                                            22

<210> SEQ ID NO 46
<211> LENGTH: 22
<212> TYPE: DNA
<213> ORGANISM: Artificial Sequence
<220> FEATURE:
<223> OTHER INFORMATION: Primer

<400> SEQUENCE: 46
acattcaaag aggcaggaca tt                                            22

<210> SEQ ID NO 47
<211> LENGTH: 22
<212> TYPE: DNA
<213> ORGANISM: Artificial Sequence
<220> FEATURE:
<223> OTHER INFORMATION: Primer

<400> SEQUENCE: 47
ttgcttcctg agcaagtcat aa                                            22

<210> SEQ ID NO 48
<211> LENGTH: 22
<212> TYPE: DNA
<213> ORGANISM: Artificial Sequence
<220> FEATURE:
<223> OTHER INFORMATION: Primer

<400> SEQUENCE: 48
tccgaaagca tgacatatca ac                                            22

<210> SEQ ID NO 49
<211> LENGTH: 24
<212> TYPE: DNA
<213> ORGANISM: Artificial Sequence
<220> FEATURE:
<223> OTHER INFORMATION: Primer

<400> SEQUENCE: 49
gcatcacccg gaggagaaaa tcgg                                          24

<210> SEQ ID NO 50
<211> LENGTH: 20
<212> TYPE: DNA
<213> ORGANISM: Artificial Sequence
<220> FEATURE:
<223> OTHER INFORMATION: Primer

<400> SEQUENCE: 50
gtcacgtgtc gcagaggagc                                               20

<210> SEQ ID NO 51
<211> LENGTH: 22
<212> TYPE: DNA
<213> ORGANISM: Artificial Sequence
<220> FEATURE:
<223> OTHER INFORMATION: Primer

<400> SEQUENCE: 51
caagtcatgc agaagttagg gg                                            22

<210> SEQ ID NO 52
<211> LENGTH: 22
<212> TYPE: DNA

```
<213> ORGANISM: Artificial Sequence
<220> FEATURE:
<223> OTHER INFORMATION: Primer

<400> SEQUENCE: 52
acccttataa agtgacctcc cc                                      22
```

COMPOSITIONS AND METHODS FOR THE TREATMENT OF PRADER-WILLI SYNDROME

021 This application is a US national phase application of International Application No. PCT/US2017/033171, filed on May 17, 2017, which claims the benefit of U.S. Provisional Patent Application No. 62/337,637, filed May 17, 2016, the disclosure of which is explicitly incorporated herein in its entirety by reference.

PRIORITY AND FEDERAL FUNDING LEGEND

This disclosure was produced in part using funds from the Federal Government under NIH grant no. HD077197 entitled, "Therapeutic Potential for Prader-Willi Syndrome." Accordingly, the Federal government has certain rights in this disclosure.

FIELD OF THE INVENTION

The present disclosure relates generally to the field of neurobiology. Specifically, the present disclosure relates to novel compositions for and methods of inhibiting histone H3K9 methylation for the treatment of genomic imprinting disorders, including Prader-Willi syndrome. More particularly, the disclosure provides compositions and methods for unsilencing the maternal copy of Prader-Willi syndrome candidate genes.

BACKGROUND OF THE INVENTION

Prader-Willi syndrome (PWS) is clinically characterized by neonatal hypotonia, childhood onset obesity, intellectual disability, and increased risk for psychosis in adults (Cassidy & Driscoll. *Eur. J Hum. Genet.* 17, 3-13 (2009)). Although paternal deficiency of the 15q11-q13 chromosomal region is well documented as the etiology of PWS, the precise molecular basis underlying the clinical features remains elusive. Several genes from the 15q11-q13 region have paternal-specific expression which is coordinately regulated by the PWS-imprinting center (PWS-IC) (Buiting, K. *Am J Med Genet C Semin Med Genet.* 154C, 365-376 (2010)). Although the specific role of MAGEL2 in PWS remains a subject of debate due to the conflicting findings in different reports (Buiting, K., et al., *Orphanet J. Rare Dis.* 9, 40 (2014); Schaaf, C. P., et al., *Nat. Genet.* 45, 1405-1408 (2013); Kanber, D., et al., *Eur J Hum Genet* 17, 582-590 (2009)), genomic copy number variant (CNV) analyses indicate that the SnoRNA cluster SNORD116 (HBII-85) located between SNRPN and UBE3A plays a critical role in PWS etiology (Sahoo, T., et al., *Nat Genet.* 40, 719-721 (2008); de Smith, A. J., et al., *Hum Mol Genet.* 18, 3257-3265 (2009); Duker, A. L., et al., *Eur J Hum Genet.* 18, 1196-1201 (2010); Bieth, E., et al., *Eur J Hum Genet.: EJHG* 23, 252-255 (2015)). SNORD116 is processed from its host transcript, a long non-coding RNA of which transcription is believed to initiate at the PWS-IC (Runte, M., et al., *Hum. Mol. Genet.* 10, 2687-2700 (2001)). Human and mouse SNORD116, including host transcripts, have the same genomic organization and imprinted expression patterns (Runte, M., et al., *Hum. Mol. Genet.* 10, 2687-2700 (2001); de los Santos, et al., *Am. J. Hum. Genet.* 67, 1067-1082 (2000); Gallagher, et al., *Am. J Hum. Genet.* 71, 669-678 (2002)), and yet the mechanism underlying the imprinted expressions of SNRPN and SNORD116 is still unclear. The PWS-IC contains a CpG island and the promoter of SNRPN and exhibits differential patterns of DNA methylation and histone modifications (Buiting, K. *Am J Med Genet C Semin Med Genet.* 154C, 365-376 (2010)). The CpG island within the PWS-IC is fully methylated in the maternal chromosome but unmethylated in the paternal chromosome (Saitoh, S., et al., *Proc Natl Acad Sci USA,* 93, 7811-7815 (1996)). Allele-specific histone modifications such as the acetylation of H3K4 (histone 3 lysine 4) and the methylation of H3K9 (histone 3 lysine 9) are also found in the PWS-IC. DNA methylation inhibitors can unsilence the expression of maternal-originated SNRPN in vitro (Fulmer-Smentek & Francke, *Hum. Mol. Genet.* 10, 645-652 (2001); Saitoh & Wada, *Am J Hum Genet.* 66, 1958-1962 (2000)). However, a similar result has not been reported in vivo.

SUMMARY OF THE DISCLOSURE

It is against the above background that the present disclosure provides certain advantages and advancements over the prior art.

Although the disclosure herein is not limited to specific advantages or functionalities, the disclosure provides compounds and a method of using those compounds for unsilencing at least one maternal copy of Prader-Willi syndrome (PWS) candidate genes, the method comprising inhibiting protein lysate methyltransferase activity by way of an interfering molecule.

In certain embodiments, the interfering molecule is of Formula I:

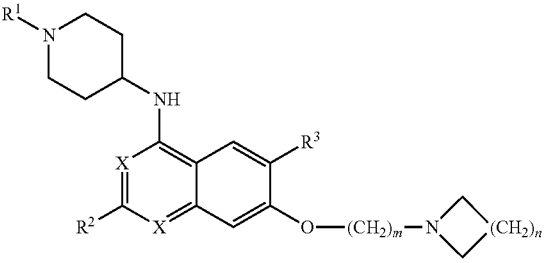

Formula I wherein
R¹ is —$C_1$-$C_8$ alkyl, —$C_3$-$C_8$ cycloalkyl, or —$C_3$-$C_8$heterocycle comprising 1-3 heteroatoms, each of which may be optionally substituted with one or more halogens;
each X is independently —CH— or —N—;
R² is —$C_3$-$C_8$ cycloalkyl or —$C_3$-$C_8$heterocycle comprising 1-3 heteroatoms, each of which may be optionally substituted with one or more alkyl groups, with one or more halogens, or with a combination thereof;
R³ is —H, —$C_1$-$C_8$ alkyl, halogen, —CN, —$CF_3$, —$NO_2$ or —$OR^5$;
wherein R⁵ is —$C_1$-$C_8$ alkyl; and
m and n are each independently 1, 2, 3, 4, or 5.

In certain embodiments of the method of unsilencing at least one maternal copy of Prader-Willi syndrome candidate genes, the interfering molecule is a G9a inhibitor.

In certain embodiments of the method of unsilencing at least one maternal copy of Prader-Willi syndrome candidate genes, the G9a inhibitor is selected from UNC617, UNC618, UNC0638, UNC0642, or any combination thereof.

In certain aspects, the disclosure provides a method of treating Prader-Willi syndrome in a subject in need thereof, the method comprising unsilencing Prader-Willi syndrome candidate genes on the maternal chromosome by administering a therapeutically effective amount of an interfering molecule.

In certain aspects, Prader-Willi syndrome is treated by by administering a therapeutically effective amount of an interfering molecule, wherein the interfering molecule is a G9a inhibitor.

In certain aspects of the method for treating Prader-Willi syndrome by administering a therapeutically effective amount of an interfering molecule, wherein the interfering molecule is a G9a inhibitor, and further wherein the G9a inhibitor is UNC617, UNC618, UNC0638, UNC0642, or any combination thereof.

Certain aspects of the disclosure provide a pharmaceutical composition comprising at least one protein lysate methyltransferase inhibitor and a pharmaceutically acceptable carrier, excipient, or adjuvant.

In certain aspects of the pharmaceutical composition, the inhibitor is UNC617, UNC618, UNC0638, UNC0642, or any combination thereof.

Certain aspects of the disclosure provide a kit useful for the treatment of Prader-Willi syndrome in a subject, the kit comprising a therapeutically effective amount of the pharmaceutical composition comprising a protein lysate methyltransferase inhibitor and instructions for use.

Certain aspects of the disclosure provide a G9a inhibitor composition (herein identified as UNC617) comprising:

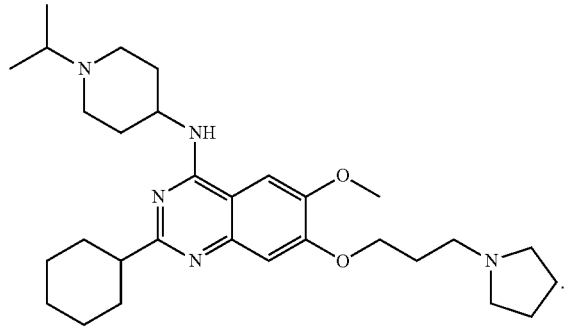 [SMILES: COc1cc2c(NC3CCN(C(C)C)CC3)nc(C3CCCCC3)nc2cc1OCCCN1CCCC1]

Specific embodiments of the invention will become evident from the following more detailed description of certain embodiments and claims.

DETAILED DESCRIPTION OF EMBODIMENTS

Figure 1:
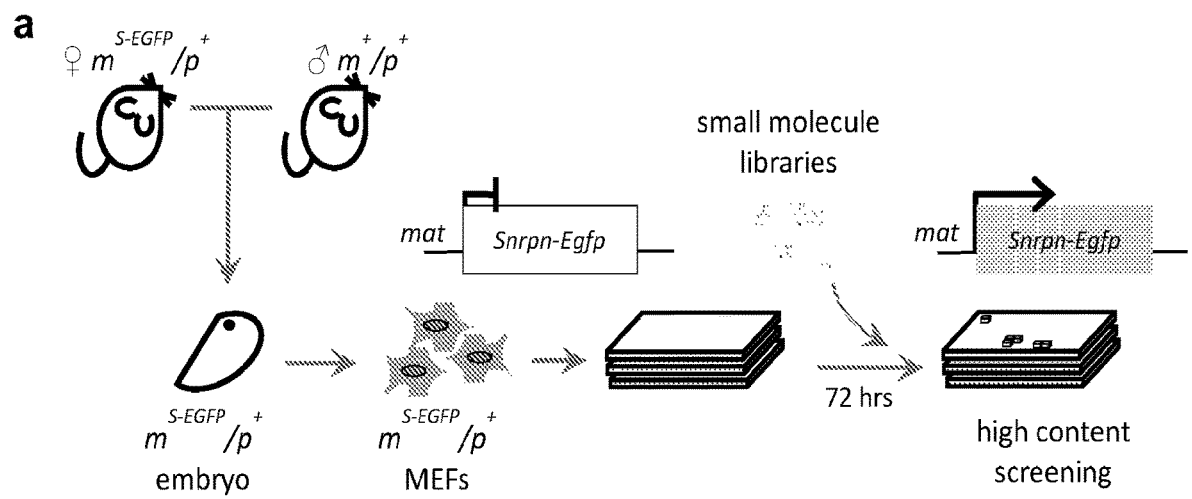
FIG. 1. Identification of small molecules that unsilence the expression of Snrpn from the maternal chromosome. (a) Screening strategy using a cell-based model. (b) High content imaging of Snrpn-EGFP following immunofluorescence staining by GFP antibody. (c) Chemical structures of some identified hits. (d) Concentration-response curves of UNC0638, UNC0642 or UNC617 in maternal Snrpn-EGFP MEFs. (e) Validation of Snrpn-EGFP mRNA expressions in G9a inhibitor- or 5-Aza-dC-treated MEFs using qRT-PCR.
Figure 1:
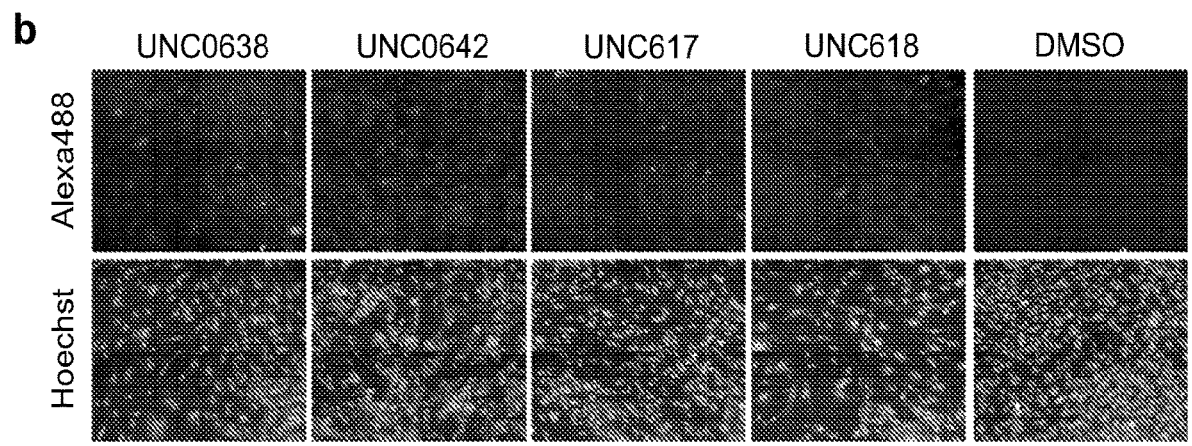
Figure 1:
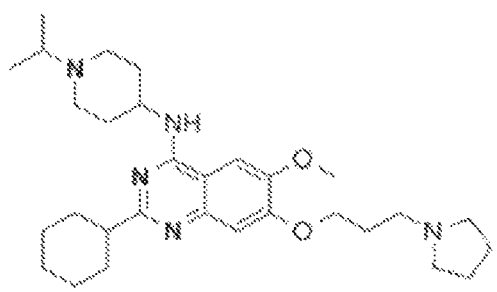
Figure 1:
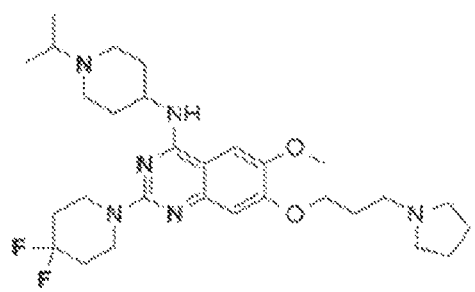
Figure 1:
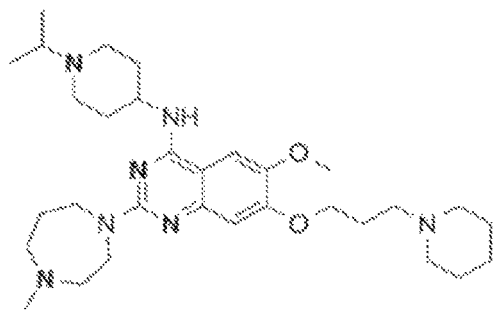
Figure 1:
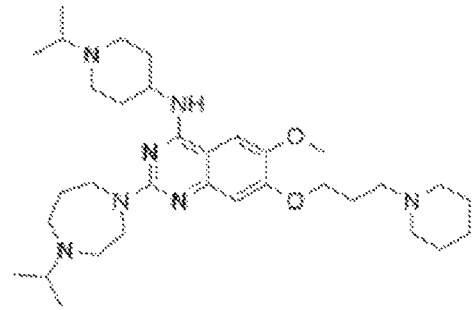
Figure 1:
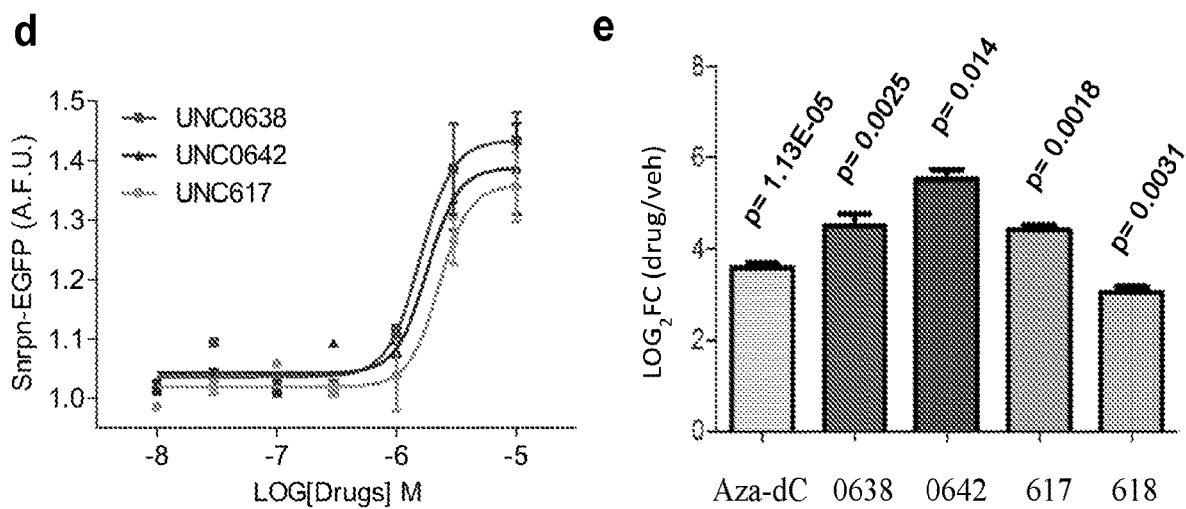

The present disclosure provides protein lysine methyltransferase inhibitor compounds that unsilence and/or activate candidate genes causing genomic imprinting disorders.

Definitions

Unless otherwise defined, all technical terms used herein have the same meaning as commonly understood by one of ordinary skill in the art to which this disclosure belongs.

The articles "a" and "an" are used herein to refer to one or to more than one (i.e. at least one) of the grammatical object of the article. By way of example, "an element" means at least one element and can include more than one element.

The term "alkyl" as used herein means a straight or branched chain hydrocarbon containing from 1 to 10 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —CH$_2$—, —CH$_2$CH$_2$—, —CH$_2$CH$_2$CHC(CH$_3$)—, —CH$_2$CH(CH$_2$CH$_3$)CH$_2$—.

The term "cycloalkyl" as used herein includes saturated and partially unsaturated cyclic hydrocarbon groups having 3 to 12 carbons unless otherwise specified. As such, "cycloalkyl" includes C3, C4, C5, C6, C7, Ce, C9, C10, C11 and C12 cyclic hydrocarbon groups. Representative cycloalkyl groups include, without limitation, cyclopropyl, cyclobutyl, cyclopentyl, cyclopentenyl, cyclohexyl, cyclohexenyl, cycloheptyl, and cyclooctyl.

The terms "heterocycle," "heterocyclyl" or "heterocyclic" refer to a ring structure having, unless otherwise specified, from 3 to 12 atoms, (3, 4, 5, 6, 7, 8, 9, 10, 11 or 12 atoms), for example 4 to 8 atoms, wherein one or more ring atoms are heteroatoms selected from the group consisting of N, O, and S, and the remainder of the ring atoms are quaternary or carbonyl carbons. The ring carbons of the heterocyclic group are optionally independently substituted. The heterocyclic group is also optionally independently substituted on nitrogen with alkyl, aryl, aralkyl, alkylcarbonyl, alkylsulfonyl, arylcarbonyl, arylsulfonyl, alkoxy carbonyl, or aralkoxy carbonyl, and on sulfur with oxo or lower alkyl. Examples of heterocyclic groups include, without limitation, epoxy, azetidinyl, aziridinyl, tetrahydrofuranyl, tetrahydropyranyl, pyrrolidinyl, piperidinyl, piperazinyl, imidazolidinyl, thiazolidinyl, dithianyl, trithianyl, dioxolanyl, oxazolidinyl, oxazolidinonyl, decahydroquinolinyl, piperidonyl, 4-piperidonyl, thiomorpholinyl, and morpholinyl.

The term "halogen" or "halo" as used herein refers to chlorine, bromine, fluorine, or iodine.

As used herein, the term "subject" and "patient" are used interchangeably and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. Preferably, the subject is a human patient.

As indicated, nucleic acid molecules of the present invention may be in the form of RNA, such as mRNA, are in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

As used herein, the term "unsilence" refers to the expressing of a gene which is silenced, repressed, or deactivated from its normally active state. In some disease states, including Prade-Willi, functional copies of proteins are not expressed, or silenced, whereas these functional copies are expressed in the non-disease state. In this disclosure, the term "unsilence" can be used interchangeably with the term "activate," "express," and the like.

The terms "activate," "express," "increase," "upregulate," "unsilence," "suppress," "inhibit," "block," "decrease," "attenuate," "downregulate," or the like, denote quantitative differences between two states, preferably referring to at least statistically significant differences between the two states.

The terms "DNA sequence encoding," "DNA encoding," and "nucleic acid encoding" refer to the order or sequence of deoxyribonucleotides along a strand of deoxyribonucleic acid. The order of these deoxyribonucleotides determines the order of amino acids along the polypeptide chain. The DNA sequence thus codes for the amino acid sequence.

The term "control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancer.

In the context of the present disclosure, the terms "cell," "cell line," "cell model," and "cell culture" are used interchangeably, and all such designations include progeny. This includes the primary subject cell, either established from a transgenic animal or created in the laboratory, and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

"Animal model," "mouse model," and "transgenic animal" are terms used interchangeably and all such terms are used to describe animals that have had an exogenous element deliberately inserted into their genome. Such animals are most commonly created by the micro-injection of DNA into the pronuclei of a fertilized egg which is subsequently implanted into the oviduct of a pseudopregnant surrogate mother. These such designations also include the primary subject animal and progeny derived therefrom without regard for the number of progeny and generations.

An "exogenous" element is defined herein to mean nucleic acid sequence that is foreign to the cell, or homologous to the cell but in a position within the host cell nucleic acid in which the element is ordinarily not found.

The term "administering" or "administered" as used herein is meant to include both parenteral and/or oral administration, all of which are described in more detail in the "pharmaceutical compositions" section below. By "parenteral" is meant intravenous, subcutaneous or intramuscular administration. In the methods of the subject disclosure, the interfering molecules of the present disclosure may be administered alone, simultaneously with one or more other interfering molecule, or the compounds may be administered sequentially, in either order. It will be appreciated that the actual preferred method and order of administration will vary according to, inter alia, the particular preparation of interfering molecules being utilized, the particular formulation(s) of the one or more other interfering molecules being utilized. The optimal method and order of administration of the compounds of the disclosure for a given set of conditions can be ascertained by those skilled in the art using conventional techniques and in view of the information set out herein. The term "administering" or "administered" also refers to oral sublingual, buccal, transnasal, transdermal, rectal, intramuscular, intravenous, intraventricular, intrathecal, and subcutaneous routes. In accordance with good clinical practice, it is preferred to administer the instant compounds at a concentration level which will produce effective beneficial effects without causing any harmful or untoward side effects.

The terms "effective amount" and "therapeutically effective amount" when used in reference to a pharmaceutical composition comprising one or more protein lysine methyltransferase inhibitor compounds refer to an amount or dosage sufficient to produce a desired therapeutic result. More specifically, a therapeutically effective amount is an amount of a protein lysine methyltransferase inhibitor compound sufficient to inhibit, for some period of time, one or more of the clinically defined pathological processes associated with the condition being treated. The effective amount may vary depending on the specific protein lysine methyltransferase inhibitor that is being used, and also depends on a variety of factors and conditions related to the patient being treated. For example, if the protein lysine methyltransferase inhibitor is to be administered in vivo, factors such as the age, weight, and health of the patient as well as dose response curves and toxicity data obtained in preclinical animal work would be among those factors considered. The determination of an effective amount or therapeutically effective amount of a given pharmaceutical composition is well within the ability of those skilled in the art.

As used herein, the term "treat" refers to the ability to make better, or more tolerable, or reduce, the clinical characterization of Prader-Willi syndrome. The terms "treating," "treatment," or "treat" as used herein refer to both therapeutic treatment and prophylactic or preventative measures. Those in need of treatment include those having the disorder as well as those prone to have the disorder or those in which the disorder is to be prevented. "Therapeutic treatment" refers to the caring for, or dealing with, a subject's Prader-Willi syndrome condition either medically or surgically, and can include "ameliorating" and/or "limiting progression." Also within the scope of the term "treating" is the acting upon a subject presenting the clinical features of Prader-Willi syndrome by the use of some agent, such as an interfering molecule, to amelioriate, improve, alter, or reduce the condition.

The terms "pharmaceutical composition" or "therapeutic composition" as used herein refer to a compound or composition capable of inducing a desired therapeutic effect when properly administered to a patient.

The term "pharmaceutically acceptable carrier" or "physiologically acceptable carrier" as used herein refers to one or more formulation materials suitable for accomplishing or enhancing the delivery of a protein lysine methyltransferase inhibitor.

One embodiment of the invention provides a pharmaceutical composition comprising a pharmaceutically acceptable carrier and a therapeutically effective amount of protein lysine methyltransferase inhibiting compound.

The term "dosage unit form" or "unit dosage" means physically discrete coherent units suitable for medical administration, each containing a daily dose or a multiple (up to four times) or a sub-multiple (down to a fortieth) of a daily dose of the active compound in association with a carrier and/or enclosed within an envelope. Whether the composition contains a daily dose, or for example, a half, a third or a quarter of a daily dose, will depend on whether the pharmaceutical composition is to be administered once or, for example, twice, three times or four times a day, respectively.

Protein Lysine Methyltransferase Inhibitor Compounds and Uses Thereof

The present disclosure provides compounds comprising interfering molecules and a method of using those compounds for the treatment of genomic imprinting disorders. Certain embodiments of the disclosure comprise compounds which activate at least one maternal copy of candidate Prader-Willi syndrome (PWS) genes. Certain embodiments of the compounds comprise at least one interfering molecule which inhibits protein lysine methyltransferase activity.

Protein lysine methyltransferases (PKMT) contain the evolutionarily conserved catalytic SET [Su(var)3-9, Enhancer-of-zeste, Trithorax] domain which catalyze the transfer of methyl groups from S-Adenosyl methionine (SAM) to e-amino group of target lysine residues by an SN-2 mechanism. Representative families of methyltransferases include, but are not limited to, EZ, SET1, SET2, SMYD, SUV39, SUV4-20, RIZ, SET8/PR-SET7, and SETT/9. Histone marks created by these enzymes can either activate transcription, for example H3K4me, or repress transcription, for example H3K27me and H2K9me. Hence the activity of these enzymes together helps in creation of bivalent chromatin marks in order to keep genes in a poised state (activation/repression).

The term "histone modification" is used herein to refer to post-translational modifications of histones. Post-translational modification of histones is a function of various enzymes that catalyze the addition of various chemical groups e.g. acetyl-, methyl-, phosphate-, ubiquitin-, etc. from one substrate to another. These modifications include, but are not limited to, arginine citrullination, arginine methylation, lysine acetylation, lysine biotinylation, lysine methylation, lysine ribosylation, lysine ubiquitination, serine/threonine/tyrosine phosphorylation. In certain embodiments, predominant targets for acetylation and methylation are the lysine and arginine residues present in the Histone peptides. The histone modifications are performed by a number of modifying enzymes including, but not limited to, methyltransferases, deiminases, acetyltransferases, biotinases, ribosylases, ubiquitinases, serine/threonine/tyrosine kinases, demethylases, deacetylases, deribosylases, deubiquitinases, serine/threonine/tyrosine phosphatases. Histone modifications play an important role in many cellular processes like DNA replication, cell cycle progression, cytokinesis, transcriptional regulation of Hox genes and tumour suppressor genes, DNA damage response, replication stress response, X chromosome inactivation, and energy homeostasis. Another significant contribution of histone modifications is the regulation of master regulators like p53 and components of the NF-kB pathway. Histone modifications are also involved in maintenance of chromatin structure by creating marks that recruit heterochromatin protein (HP1) in order to initiate the process of heterochromatinisation.

In certain aspects, the method of activating at least one maternal copy of Prader-Willi syndrome candidate genes comprises inhibiting G9a activity. G9a (UniprotKB Accession Q96KQ7; also known as KMT1C or EHMT2) and GLP (UniprotKB Accession Q9H9B1; also known as EHMT1) are both protein lysine methyltransferases (PKMT) known to modulate the transcriptional repression of a variety of genes via dimethylation of Lys9 on histone H3. In certain aspects of the disclosure, the method of activating at least one maternal copy of Prader-Willi syndrome candidate genes comprises inhibiting G9a activity whereby the inhibition of G9a activity comprises inhibiting the methylation of the Histone H3 protein. In certain aspects, the method comprises inhibiting the methylation of Histone H3 at lysine 9.

In certain embodiments, the method comprises inhibiting the methylation of H3K9 through a selective reduction of demethylation of histone 3 lysine 9.

In certain embodiments, the method of unsilencing at least one maternal copy of Prader-Willi syndrome candidate genes, the PWS candidate genes are located on the 15q11-q13 region between the MAGEL2 and UBE3A genes.

In certain aspects, the method of unsilencing at least one maternal copy of Prader-Willi syndrome candidate genes, the PWS candidate genes comprise MAGEL2, NDN, SNRPN, and SnoRNAs genes.

In certain aspects of the method of unsilencing at least one maternal copy of Prader-Willi syndrome candidate genes, the SnoRNAs gene comprises SNORD116, and/or SNORD115.

In certain embodiments of the method of unsilencing at least one maternal copy of Prader-Willi syndrome candidate genes, the interfering molecule is a G9a inhibitor.

In certain embodiments of the method of unsilencing at least one maternal copy of Prader-Willi syndrome candidate genes, the G9a inhibitor is selected from UNC617, UNC618, UNC0638, UNC0642, or any combination thereof. As used herein, "any combination thereof" or "combination" is intended to refer to any combination of 2 or more inhibitors, in any ratio. Thus, in non-limiting examples, a combination may include UNC617 and UNC618, a combination may include UNC617, UNC618, and UNC638, or a combination may include UNC617, UNC618, UNC0638, or UNC0642. The combination includes the use of multiple inhibitors either sequentially or concurrently.

In certain embodiments, the methods of unsilencing at least one maternal copy of Prader-Willi syndrome candidate genes may be achieved through use of a combination of an interfering molecule as disclosed herein and an inhibitor of DNA methylation. The inhibitor of DNA methylation may include, but is not limited to, azacytidine and decitabine.

In certain aspects, the disclosure provides a method of treating Prader-Willi syndrome in a subject in need thereof, the method comprising unsilencing Prader-Willi syndrome candidate genes on the maternal chromosome by administering a therapeutically effective amount of an interfering molecule, wherein the methylation of H3K9 is reduced.

In certain aspects of the method for treating Prader-Willi syndrome by administering a therapeutically effective amount of an interfering molecule, the interfering molecule is a G9a inhibitor.

In certain aspects of the method for treating Prader-Willi syndrome by administering a therapeutically effective amount of an interfering molecule, the interfering molecule is a G9a inhibitor, and the G9a inhibitor is UNC617, UNC618, UNC0638, UNC0642, or any combination thereof.

In certain aspects of the method for treating Prader-Willi syndrome by administering a therapeutically effective amount of an interfering molecule, the interfering molecule is a G9a inhibitor, and the therapeutically effective amount of interfering molecule unsilences at least one gene within the PWS critical region (or PWS-IC-controlled region).

In certain aspects of the method for treating Prader-Willi syndrome by administering a therapeutically effective amount of an interfering molecule, the interfering molecule is a G9a inhibitor, the therapeutically effective amount of interfering molecule unsilences at least one gene within the PWS critical region (or PWS-IC-controlled region), and the at least one unsilenced gene within the PWS critical region is SNORD116.

In certain aspects of the method for treating Prader-Willi syndrome in a subject in need thereof by administering a therapeutically effective amount of an interfering molecule, methylation of H3K9 is reduced, wherein the subject is a mammal.

In certain aspects of the method for treating Prader-Willi syndrome in a subject in need thereof by administering a therapeutically effective amount of an interfering molecule, methylation of H3K9 is reduced, wherein the subject is a human.

In certain embodiments, the methods for treating Prader-Willi syndrome in a subject in need thereof may be achieved through the administration of a combination of an interfering molecule as disclosed herein and an inhibitor of DNA methylation. The inhibitor of DNA methylation may include, but is not limited to, azacytidine and decitabine.

One aspect of the disclosure comprises an interfering molecule. As used herein, an interfering molecule refers to any molecule that is capable of disrupting histone modification. In preferred embodiments, the "interfering molecule" is capable of interfering with histone H3 modification. Certain embodiment, the interfering molecule is capable of interfering with histone H3 lysine 9 modification carried out by protein lysine methyltransferases.

In certain embodiments, the interfering molecule may be a small molecule. In such embodiments, the small molecules generally have a molecular weight of approximately 600 Da or less and may include, but are not limited to amino acids, monosaccharides, oligosaccharides, nucleotides, olionucleotides, salt compositions, and their derivatives. In certain embodiments, the small molecules are capable of crossing the blood brain barrier.

In certain embodiments, the interfering molecule is a protein lysine methyltransferase inhibitor. As used herein, protein lysine methyltransferase inhibitor refers to a compound creating a difference between two states, one state comprising a protein lysine methyltransferase (PKMT) and the other state comprising a PKMT and a PKMT inhibitor. In the latter state, there is a statistically significant decrease in the activity of the PKMT when compared to the first state. PKMT inhibitors can exhibit substrate-competitive behavior, showing competition with the peptide substrate, showing the $K_m$ of the peptide increases linearly with the PKMT inhibitor concentration.

In one aspect of the disclosure, the interfering molecule is of Formula I:

Formula I

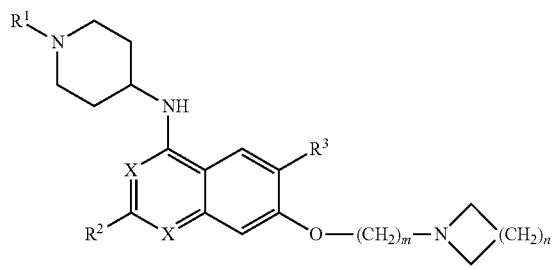

wherein
$R^1$ is —$C_1$-$C_8$ alkyl, —$C_3$-$C_8$ cycloalkyl, or —$C_3$-$C_8$ heterocycle comprising 1-3 heteroatoms, each of which may be optionally substituted with one or more halogens;

each X is independently —CH— or —N—;

$R^2$ is —$C_3$-$C_8$ cycloalkyl or —$C_3$-$C_8$ heterocycle comprising 1-3 heteroatoms, each of which may be optionally substituted with one or more alkyl groups, with one or more halogens, or with a combination thereof;

$R^3$ is —H, —$C_1$-$C_8$ alkyl, halogen, —CN, —$CF_3$, —$NO_2$ or —$OR^5$;

wherein $R^5$ is —$C_1$-$C_8$ alkyl; and m and n are each independently 1, 2, 3, 4, or 5.

In certain embodiments, $R^1$ is alkyl. In certain embodiments, $R^1$ is isopropyl.

In certain embodiments, both occurances of X are —N—.

In certain embodiments, $R^2$ is a 6-7 membered cycloalkyl or heterocyclic ring. In certain embodiments, $R^2$ is substituted with one or more halogens. In certain embodiments, $R^2$ is substituted with $C_1$-$C_3$ alkyl, including but not limited to methyl and isopropyl. In certain embodiments, $R^2$ is selected from the group consisting of:

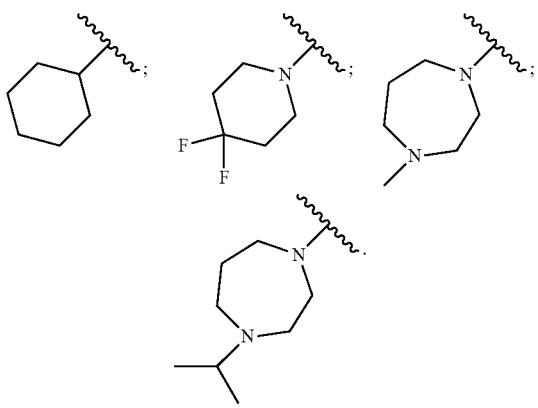

In certain embodiments, $R^3$ is —$OCH_3$.

In certain embodiments, m is 3 and n is 2 or 3.

It will be understood by one of skill in the art that the various embodiments of Formula I disclosed herein may be combined in any manner, even if such combinations are not specifically delineated.

In certain emodiments, the interfering molecule is of Formula II:

Forumula II

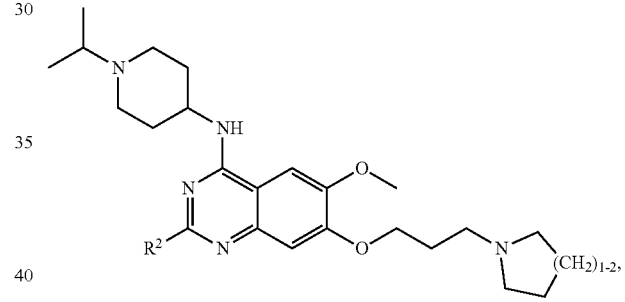

wherein $R^2$ is as defined above.

The interfering molecules of the invention include pharmaceutically acceptable salts, esters, amides, and prodrugs thereof, including but not limited to carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention.

Certain embodiments disclosed herein include inhibitors to the PKMT G9a. These G9a inhibitors include, but are not limited to, UNC617, UNC618, UNC0638, UNC0642, or combinations thereof. The structures of UNC617, UNC618, UNC0638, and UNC0642 are shown in FIG. 1c.

UNC617 (MW=554.4177) is an inhibitor of G9a showing a similar potency to G9a as UNC0638 (FIG. 1e).

UNC618 (MW=523.54) is an inhibitor of G9a displaying an IC50=6 nM. See Liu, F., et al., *J. of Med. Chem.*, 54, 6139-6150 (2011).

UNC0638 (MW=509.735) is a potent, substrate-competitive inhibitor of G9a (IC50<15 nM, Ki=3 nM) and the closely related GLP (IC50=19 nM). UNC0638 is selective for G9a and GLP over a wide range of epigenetic and non-epigenetic targets. UNC0638 is highly active in cells: at 250 nM concentration, it reduces the levels of H3K9me2 by ~60-80% in a variety of cell lines, similar to the reductions seen for shRNA knockdown of G9a and GLP, and modulates expression of known G9a-regulated genes (see Vedadi, M., et al., Nat. Chem. Biol., 7, 566-574 (2011)).

UNC0642 (MW=529.64) is a potent and selective inhibitor of G9a and GLP shown in biochemical and cellular assays with an IC50<2.5 nM. UNC0642 is also selective for G9a and GLP over several methyltransferases (greater than 2000-fold over PRC2-EZH2 and greater than 20,000 over 13 other methyltransferases) as well as over a broad range of kinases, GPCRs, ion channels, and transporters (greater than 300-fold selectivity). UNC0642 exhibits high potency for H3K9me2 mark, low cell toxicity, and suitable separation of functional potency and cell toxicity in a several cell lines. UNC0642 also shows pharmacokinetic properties superior to UNC0638, such as, central nervous system penetration (see Liu, F., et al., J. of Med. Chem., 56, 8931-8942 (2013)).

Certain aspects of the present disclosure provide a G9a inhibitor composition (herein identified as UNC617) comprising:

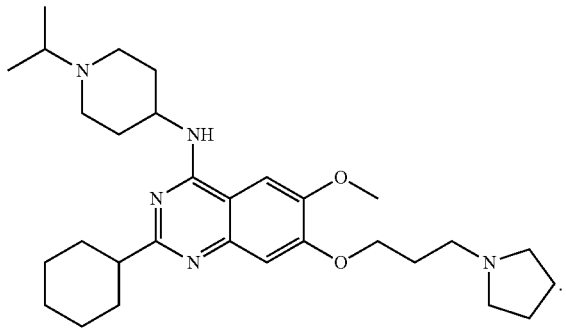 [SMILES: COc1cc2c(NC3CCN(C(C)C)CC3)nc(C3CCCCC3)nc2cc1OCCCN1CCCC1]

Additional aspects of the disclosure provide a G9a inhibitor composition comprising UNC617 and further comprising a pharmaceutically acceptable salt thereof.

Pharmaceutical Compositions

Certain aspects of the disclosure provide a pharmaceutical composition comprising at least one G9a inhibitor for inhibiting methylation of H3K9 in a subject with Prader-Willi syndrome and a pharmaceutically acceptable carrier, excipient, or adjuvant.

Certain aspects of the disclosure provide a pharmaceutital composition comprising at least one G9a inhibitor for inhibiting methylation of H3K9 in a subject with Prader-Willi syndrome and the G9a inhibitor can be UNC617, UNC618, UNC0638, UNC0642, or any combinations thereof.

In certain aspects, disclosed herein is a pharmaceutical composition comprising the disclosed composition for unsilencing and activating candidate Prader-Willi genes. In certain embodiments the pharmaceutical composition comprises the compositions disclosed herein and a pharmaceutically acceptable carrier, excipient or adjuvant.

In some embodiments, the pharmaceutical compositions of the disclosure may further comprise a DNA methylation inhibitor.

Acceptable formulation materials preferably are nontoxic to recipients at the dosages and concentrations employed. The pharmaceutical composition can contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides, disaccharides, and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, polyethylene glycol (PEG), sorbitan esters, polysorbates such as polysorbate 20 and polysorbate 80, Triton, trimethamine, lecithin, cholesterol, or tyloxapal); stability enhancing agents (such as sucrose or sorbitol); tonicity enhancing agents (such as alkali metal halides, preferably sodium or potassium chloride, mannitol, or sorbitol); delivery vehicles; diluents; excipients and/or pharmaceutical adjuvants (see, for example, Remington's Pharmaceutical Sciences, 18th Edition, (A. R. Gennaro, ed.), 1990, Mack Publishing Company).

Additional pharmaceutical compositions of the invention will be evident to those skilled in the art, including formulations involving G9a inhibitor compounds in sustained- or controlled-delivery formulations. Techniques for formulating a variety of other sustained- or controlled-delivery means, such as liposome carriers, bio-erodible microparticles or porous beads and depot injections, are also known to those skilled in the art. Additional examples of sustained-release preparations include semipermeable polymer matrices in the form of shaped articles, e.g. films, or microcapsules. Sustained release matrices can include polyesters, hydrogels, polylactides, copolymers of L-glutamic acid and gamma ethyl-L-glutamate, poly(2-hydroxyethyl-methacrylate), ethylene vinyl acetate, or poly-D(–)-3-hydroxybutyric acid. Sustained-release compositions can also include liposomes, which can be prepared by any of several methods known in the art.

Pharmaceutical compositions of the invention to be used for in vivo administration typically must be sterile. This can be accomplished by filtration through sterile filtration membranes. Where the composition is lyophilized, sterilization using this method can be conducted either prior to, or following, lyophilization and reconstitution. The composition for parenteral administration can be stored in lyophilized form or in a solution. In addition, parenteral compositions generally are placed into a container having a sterile access port, for example, an intravenous solution bag or vial having a stopper pierceable by a hypodermic injection needle.

Once the pharmaceutical composition has been formulated, it can be stored in sterile vials as a solution, suspension, gel, emulsion, solid, or as a dehydrated or lyophilized powder. Such formulations can be stored either in a readyto-use form or in a form (e.g., lyophilized) requiring reconstitution prior to administration.

In a non-limiting example, the G9a inhibitor UNC0642 was administered to mice to examine the pharmacological effects thereof. For intraperitoneal injection, the solution of UNC0642 was prepared to the concentration of 0.5 mg/ml in sterile saline, and was administered to mice daily at a volume of 5-10 microliter per g body weight. The dosage and duration of UNC0642 used is 2.5-5.0 mg/kg and 5-7 consecutive injections. The dosage and duration vary depending on the age and condition of animals. For example, neonatal treatment of PWS mice used 2.5 mg/kg and 5 daily injections starting at 1 week-old, and adult mice treatment used 5 mg/kg and 7 daily injections.

Certain aspects of the disclosure encompass kits for producing a single-dose administration unit. Certain aspects of the disclosure provide a kit useful for the treatment of Prader-Willi syndrome in a subject. The kit comprising both a therapeutically effective amount of a pharmaceutical composition comprising a G9a inhibitor for the methylation of H3K9 and instructions for use. The kits can each contain both a first container having a dried protein and a second container having an aqueous formulation. Also included within the scope of this disclosure are kits containing single and multi-chambered pre-filled syringes (e.g., liquid syringes and lyosyringes).

As described herein, the effective amount of a G9a inhibitor pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the G9a inhibitor is being used, the route of administration, and the size (body weight, body surface, or organ size) and condition (the age and general health) of the patient. Accordingly, the clinician can titer the dosage and modify the route of administration to obtain the optimal therapeutic effect. A typical dosage can range from about 0.1 µg/kg to up to about 100 mg/kg or more, depending on the factors mentioned above. In other embodiments, the dosage can range from 0.1 µg/kg up to about 100 mg/kg; or 1 µg/kg up to about 100 mg/kg; or 5 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, up to about 100 mg/kg.

Dosing frequency will depend upon the pharmacokinetic parameters of the G9a inhibitor in the formulation being used. Typically, a clinician will administer the composition until a dosage is reached that achieves the desired effect. The composition can therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages can be ascertained through use of appropriate dose-response data.

The route of administration of the pharmaceutical composition is in accord with known methods, e.g., orally; through injection by intravenous, intraperitoneal, intracerebral (intraparenchymal), intracerebroventricular, intramuscular, intraocular, intraarterial, intraportal, or intralesional routes; by sustained release systems; or by implantation devices. Where desired, the compositions can be administered by bolus injection or continuously by infusion, or by implantation device.

The composition can also be administered locally via implantation of a membrane, sponge, or other appropriate material onto which the desired molecule has been absorbed or encapsulated. Where an implantation device is used, the device can be implanted into any suitable tissue or organ, and delivery of the desired molecule can be via diffusion, timed-release bolus, or continuous administration.

EXAMPLES

The Examples which follow are illustrative of specific embodiments of the invention, and various uses thereof. They set forth for explanatory purposes only, and are not to be taken as limiting the invention.

General Methods

Cell Culture

To generate primary mouse embryonic fibroblasts (MEFs) carrying maternal Snrpn-EGFP ($m^{S-EGFP}/p^+$), Snrpn-EGFP/+ heterozygous females were crossed with wild-type males and embryos were isolated at E12.5 to E14.5 day. In addition, MEFs carrying paternal Snrpn-EGFP ($m^+/p^{S-EGFP}$) were isolated from the embryos of wild-type females crossing with Snrpn-EGFP/+ heterozygous males. Human PWS fibroblasts were obtained from Baylor College of Medicine cell repository and NIGMS Human Genetic Mutant Cell Repository. Mouse embryonic fibroblast cells were maintained in Dulbecco's modified Eagle's media (Gibco 11995-065) supplemented with 10% fetal bovine serum (Gibco 10082-147), 1% Gentamicin (Gibco 15710-064), 1% Glutamine (Gibco 25030-149), 1% non-essential amino acid (Gibco 11140-050), 0.1% beta-mercaptoethanol (Gibco 21985-023), 100 Units/mL penicillin and 100 µg/mL streptomycin (Gibco 15240-062) at 37° C. and 5% CO2. Human fibroblast cells were maintained in Minimum Essential Medium Alpha media (Gibco 12571-063) supplemented with 10% fetal bovine serum (Gibco 10082-147), 1% L-Glutamine (Gibco 25030-081), 100 Units/mL penicillin and 100 micrograms/mL streptomycin (Gibco 15240-062) at 37° C. and 5% $CO_2$.

High Content Screening of Small Molecule Libraries

Figure 2:
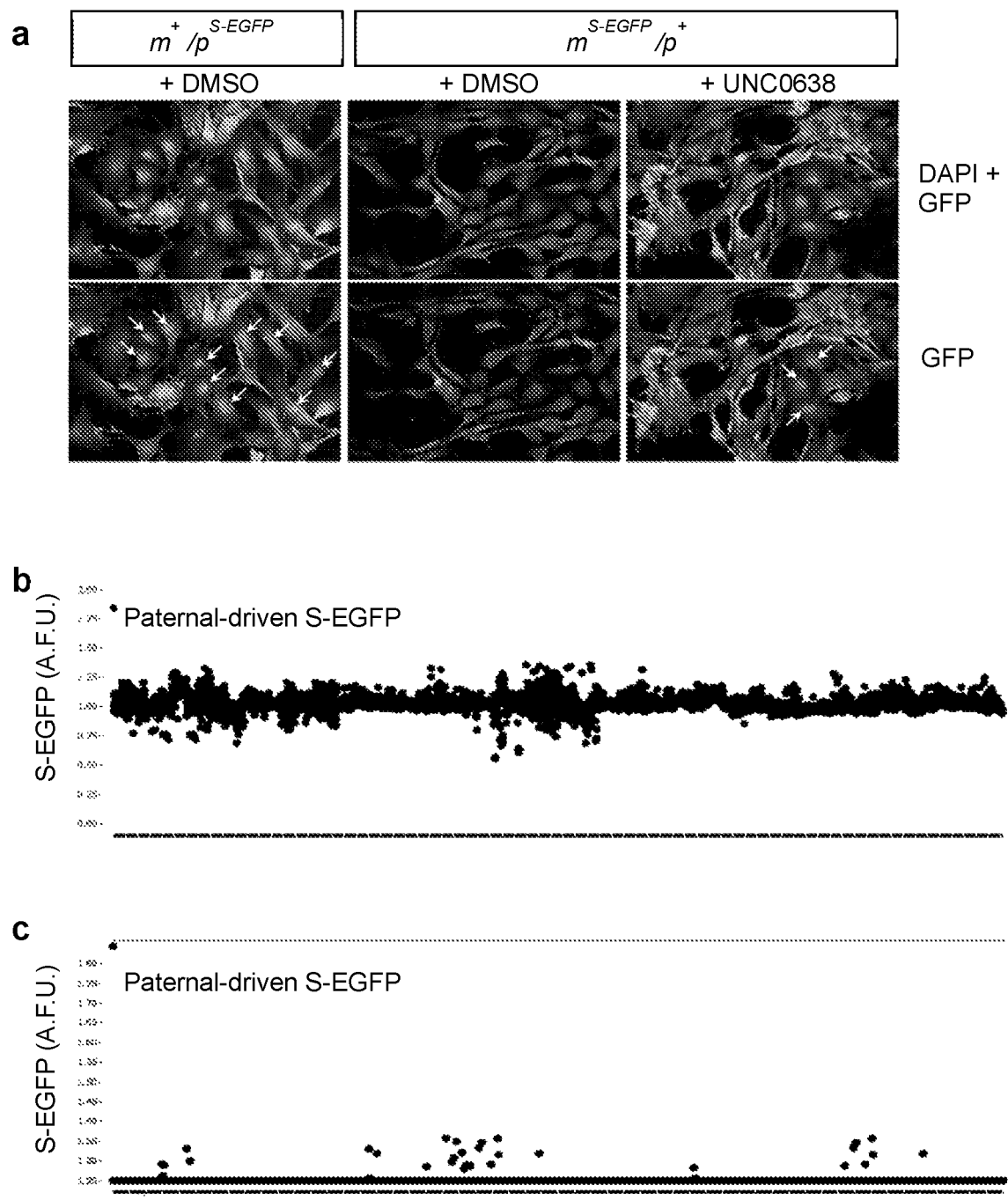
FIG. 2. Synthesis of UNC617. Where (a) is 1-methyl hoomopiperazine, $CF_3COOH$, i-PrOH, 160° C., 72%.

High content screenings of small molecules were performed as described in Huang, et al. *Nature* 481, 185-189 (2012). HCS comprises a 384-well high-content screen using primary mouse embryonic fibroblasts (MEFs) from $m^{S-EGFP}/p^+$, and searched for drug-like molecules that could unsilence the maternal S-EFGP allele. As seen in FIG. 1. FIG. 2, then shows the use of paternal expression of Snrpn-EGPF in $m^+/p^{S-EGFP}$ MEFs as a positive control and vehicle treated $m^{S-EGFP}/p^+$ MEFs as a negative control, the unsilencing of Snrpn-EGFP was determined by nuclear EDFP signal in UNC0638 treated $m^{S-EGFP}/p^+$ MEFs. To perform the screen, primary MEFs were isolated from E12.5-14.5 embryos of $m^{S-EGFP}/p^+$ and cultured for 7 days in Dulbecco's modified Eagle's media supplemented with 10% fetal bovine serum, 100 Units/mL penicillin and 100 µg/mL streptomycin, at 37° C. and 5% $CO_2$. One day before treatment with small molecules, 5,000 cells per well were plated onto 384-well plates. The cells were then treated with compounds (10 µM for 72 hours) from multiple small molecule libraries (FIG. 1*f* and FIG. 2). In total, 9,157 small molecules were screened in quadruplicate, normalizing values to vehicle-treatment (0.2% DMSO) (Table 1). The unsilencing of Snrpn-EGFP was determined three days after drug treatment. The immunofluorescence-processed fibroblasts were imaged for Hoechst and Alexa Fluor 488 fluorescence using a BD Pathway 855 high content imaging microscope. Antibody-enhanced Snrpn-EGPF fluorescence intensity was determined in drug-treated cells individually and normalized to cells treated with vehicle control. In order to identify potentially active compounds, an arbitrary cutoff of 125% was used where 100% indicates basal fluorescence in the vehicle-treated MEFs. Analysis was performed using Cell Profiler with custom macro and algorithms. Potential active drugs were defined as the increase in drug-mediated EGFP fluorescence consistently observed across quadruplicate wells and minimal or no cytotoxicity measured by Hoechst-stained nuclear structure (and the changes in total number of cells). After initial validation of all potential active drugs (e.g., to determine whether active compounds show inherent fluorescence, the wild-type fibroblasts were also treated), only effective hit compounds further validated in dose-response tests to determine relative efficacy ($E_{max}$) and potency ($EC_{50}$). The dose-response results were analyzed by using Graphpad Prism (Graphpad Software). The calculated $EC_{50}$ values (potencies) and estimated $E_{max}$ (efficacy, Y-value top plateau) enabled comparative analyses of the relative potency and efficacy of the identified compounds.

In Vitro and In Vivo Drug Treatment

Human fibroblast cells were grown to ~80% confluence and were treated with compounds (UNC617, UNC0638, and UNC0642 at 4 μM; UNC618 at 8 μM; or 5-aza-dC at 10 μM final concentration) diluted in culture medium for 72 hours. For the treatment in PWS animal model, $m^+/p^{\Delta S-U}$ litters were given UNC0642 (2.5 mg/kg) diluted in isotonic saline solution (PBS) containing 0.02% DMSO by daily intraperitoneal (i.p.) injection starting at P7 and then five following days. For testing long lasting drug effects, the 6 week-old $m^{S-EGFP}/p^+$ mice were treated daily by i.p. injection for seven consecutive days.

General Chemistry Procedures

HPLC spectra for UNC617 was acquired using an Agilent 6110 Series system with UV detector set to 254 nm. Samples (5 μl) were injected onto an Agilent Eclipse Plus 4.6×50 mm, 1.8 M, C18 column at room temperature. A linear gradient from 10% to 100% B (MeOH+0.1% acetic acid) in 5.0 min was followed by pumping 100% B for another 2 min with A being H2O+0.1% acetic acid. The flow rate was 1.0 m/min. Mass spectra (MS) data was acquired in positive-ion mode using an Agilent 6110 single-quadrupole mass spectrometer with an electrospray ionization (ESI) source. High-resolution mass spectra (HRMS) was acquired using an Aglient 6210 LCMS orthogonal-axis time-of-flight (TOF) mass spectrometer. Nuclear magnetic resonance (NMR) spectra was recorded at Varian Mercury spectrometer with 400 MHz for proton (1H NMR) and 100 MHz for carbon (13C NMR); chemical shifts are reported in p.p.m. (6). Preparative HPLC was performed on Agilent Prep 1200 series with UV detector set to 220 nm. Samples were injected onto a Phenomenex Luna 75×30 mm, 5 M, C18 column at room temperature. The flow rate was 30 ml/min. A linear gradient with 10% of MeOH (A) in 0.1% TFA in H2O (B) to 100% of MeOH (A) was used. HPLC was used to establish the purity of target compounds.

Immunoblotting

Western blot analysis was performed as previously described by Wang, et al., *Molecular Autism* 5, 30 (2014). Briefly, total protein was extracted from collected tissues (liver and brain) using modified RIPA buffer (1× PBS, 1% Triton X-100, 0.1% SDS, 2 mM EDTA, and protease inhibitors). SDS-PAGE resolved 25 μg of total proteins and they were transferred to polyvinylidene difluoride (PVDF) membranes. The PVDF membranes were blocked with BLOTTO (5% skim milk and 0.1% Tween-20 in 1× TBS buffer), and incubated with primary target antibodies, rabbit anti-Snrpn (Protein Tech, cat. no. 11070-1-AP) at 1:400, and rabbit anti-Ube3a (Bethyl Lab, cat. no. A300-352A-T) at 1:1,000 working concentration in BLOTTO at 4° C. overnight. The next day, following incubation with horseradish peroxidase-conjugated secondary antibodies, the membranes were incubated with a Pierce chemiluminescent substrate and exposed to X-ray film or imaged by AI600 (GE Healthcare Life Science).

Immunocytochemistry

Immunofluorescence staining was performed to detect any up-regulated Snrpn-EGFP. Three days after drug treatment, the cells were fixed at 4% paraformaldehyde at room temperature for 10 min, followed by rinsing with 1× PBS. The cells were permeabilized with 0.5% Triton X-100 in 1× PBS at room temperature for 10 min, followed by blocking with 5% normal goat serum in 0.1% Triton X-100 in 1× PBS at room temperature for 30 minutes. Primary rabbit anti-GFP antibody (1:1000, Novus Biologicals cat. no. NB100-1770) was incubated at 4° C. overnight. The next day, the cells were rinsed with 1× PBS and incubated with goat anti-rabbit Alexa Fluor 488 (Invitrogen cat. no. A-11008) and Hoechst at room temperature. One hour after incubation, the cells were rinsed with 1× PBS and imaged for Hoechst and Alexa Fluor 488 fluorescence using a BD Pathway 855 high content imaging microscope.

Cell Viability Assays

Cell viability was measured by fluorescence using CellTox™ Green Cytotoxicity Assay (Promega, cat. no. G8741) according to the manufacturer's instructions.

Histopathological Analysis

Brain, liver, lung, kidney and heart tissues from 3-month-old mice were fixed in 10% neutral buffered formalin (NBF: 10 ml of Formalin (37% stock), 90 ml of deionized water, 4 g/liter of NaH2PO4, 6.5 g/liter Na2HPO4), embedded in paraffin, sectioned at 5 μm, stained with hematoxylin and eosin, and images examined by a board-certified toxicological pathologist.

Blood Chemistry and Hematological Analysis

Blood was collected from 3-month-old mice into microcontainers or hematology assay tubes using jugular vein bleeding puncture. A serum metabolic panel was obtained using the Heska Dry Chem analyzer (Cuattro Veterinary USA). The metabolic panel contained chem and electrolyte, liver and kidney functions. For hematology analysis, we tested whole blood using Procyte (IDEXX).

RT-PCR and qRT-PCR

For reverse-transcription PCR (RT-PCR) and quantitative real time RT-PCR (qRT-PCR), first total RNA was extracted from the fibroblasts and/or collected tissues (liver and brain) using Direct-zol RNA Miniprep kit (Zymo Research cat. no. R2070). 2 μg of total RNA was directly used for single strand cDNA synthesis with Superscript III reverse transcriptase (Invitrogen cat. no. 18080-093) according to the manufacturer's protocols. The conditions for RT-PCR were 95° C./5 min, 35-40 cycles of 95° C./30 sec, 56-60° C./60 sec, 72° C./60 sec. Quantification of target gene expression was performed in a LightCycler480 instrument (Roche) using SsoAdvanced Universal SYBR green Supermix (Bio-rad cat. no. 172-5271) according to the manufacturer's instructions. See Table 4 for primer sequences and conditions used for experiments for RT-PCR, qRT-PCR, bisulfite genomic sequencing, ChIP-qPCR, and chromatin accessibility assay.

Bisulfite Genomic Sequencing

Genomic DNA was isolated from human PWS fibroblasts or mouse tissues. DNA (1 μg) was then treated by bisulfite using the Epi-Tect bisulfite kit (Qiagen), and 125 ng input DNA was used per PCR amplification. PCR products were sub-cloned into pGEM-T easy vector (Promega) and an average of 15 clones were sequenced. DNA sequencing results were analyzed using BISMA web-based analysis platform with a setting for individual clones with <95% bisulfite conversion and <90% sequence identity to be excluded in the analysis.

Chromatin Immunoprecipitation Assays

Histone methylations on the SNRPN locus in human fibroblasts were analyzed by chromatin immunoprecipitation assay (ChIP) using the protocol as previously reported (see Fulmer-Smentek et al., *Human molecular genetics* 10, 645-652 (2001)). ChIP assay was performed using ChIP-IT Express magnetic kit (Active Motif) according to the manufacturer's instructions with modification for the fixation and reverse-crosslinking steps. Briefly, native chromatin was prepared without fixation and enzymatic digestions to average 150-500 bp sized chromatin. 20 µg of chromatin was added to the specific antibodies (2 µg) or species control isotype antibodies for each immunoprecipitation reaction. The antibody-chromatin complexes were bound to protein G magnetic beads for recovering chromatin immunoprecipitates. RNase- and proteinase K-treated DNA was purified using PCR purification columns (Promega). DNA recovery was quantified by real time PCR performed on the LightCycler480 instrument (Roche) using SsoAdvanced Universal SYBR green Supermix (Biorad). Antibodies were anti-rabbit acetylated H3 (Millipore 06-599), anti-mouse monoclonal Histone H3 dimethyl K9 (Abcam 1220) and Histone H3 trimethyl K9 (Millipore, 07-442) antibodies. qPCR reactions were performed with the following cycling parameters: at 95° C./5 min followed by 40 cycles of 95° C./30 sec, 60° C./60 sec. Data was normalized to the total input.

Chromatin Accessibility Assays

Chromatin accessibility assay was performed to investigate whether G9a inhibitors change open/close state of the imprinted cluster in the PWS-IC region according to Pai, C.C., et al. *Nature communications* 5, 4091 (2014) with slight modifications. Briefly, 3 days after drug treatment in human PWS fibroblasts, the cells were harvested and lysed with lysis buffer (0.5% NP-40, 15 mM Tris-HCl [pH 7.4], 0.15 mM Spermidine, 0.5 mM Spermine, 15 mM NaCl, 60 mM KCl, 1 mM DTT, 0.1 mM PMSF, 0.5M Sucrose, Protease and Phosphatase inhibitor cocktail (Roche)). The lysed cells were collected by centrifugation (3000 RPM/10 min/4° C.) and rinsed with digestive buffer (15 mM Tris-HCl [pH 7.4], 15 mM NaCl, 60 mM KCl, 4 mM MgCl2, 1 mM DTT, 0.1 mM PMSF, 0.35M Sucrose). After rinsing the cell pellets, MNase (NEB) was added to digest open status of chromatins, followed by genomic qPCR to determine changes in amount of SNRPN and other imprinted genes.

Gross Neurological Screening

General health of mice was evaluated using a modified version of standard test battery for behavioral phenotyping (see 57). Observational assessment included the evaluation of body weight, body core temperature, overt behavioral signs (coat appearance, body posture and secretary signs) and sensory functions (visual ability, audition, tactile perception and vestibular function). Table 6 indicates the mouse sex and age information.

Statistical Analysis

Graphpad Prism (Graphpad Software) was used for the statistical analysis. Student t-tests were used to examine the statistical significance between groups (vehicle controls vs. drug treated experiments). $p<0.05$ was considered statistically significant. For the comparison of survival rate after drug treatment, Kaplan-Meier Log rank test was used. All data were expressed as mean±s.e.m. The number of mice (or cell cultures) in each experimental group was indicated in text. No data points were excluded.

Examples Illustrative of Specific Embodiments

The Examples which follow are illustrative of specific embodiments of the invention, and various uses thereof. They set forth for explanatory purposes only, and are not to be taken as limiting the invention.

Example 1

Identification of Small Molecules that Activate the Expression of SNORD116 from the Maternal Chromosome It is not feasible to design a screen for noncoding RNA. Alternatively, SNRPN/Snprn is paternally expressed but maternally silenced in all human and mouse tissues. The allele-specific expression of human SNRPN is regulated by the PWS-IC, which also controls the expression of host transcripts for SnoRNAs, including the SNORD116 cluster between SNRPN and UBE3A. see Le Meur, E. et al., *Dev. Biol.* 286, 587-600 (2005). Thus, the Snrpn-EGFP fusion protein (hereafter S-EGFP) was used as a marker for high content screening (HCS). It was determined that small molecules that can unsilence S-EGFP would also be effective in reactivating the host transcript of SNORD116. Thus, mouse embryonic fibroblasts (MEFs) were established from mice carrying S-EGFP inherited either maternally ($m^{S-EGFP}/p^+$) or paternally ($m^-/p^{S-EGFP}$) as previously described by Wu, M. Y., et al. *Genes & development* 20, 2859-2870 (2006). S-EGFP was confirmed to be expressed in $m^+/p^{S-EGFP}$ and silenced in $m^{S-EGFP}/p^+$ MEFs (FIG. 2a). The MEFs of $m^{S-EGFP}/p^+$ were then subjected to a HCS using the protocol previously described Huang, H.S., et al., *Nature* 481, 185-189 (2012) (FIG. 1a). Screening was performed in quadruplicate using 13 small-molecule libraries (10 µM in 0.2% DMSO; Table 1), chosen to ensure chemical diversity and pharmacological and bilogical activity. Using an initial arbitrary cut-off of 125% (100% indicates basal fluorescence in the vehicle-treated MEFs), out of 9,157 compounds (FIG. 2b), 32 potentially active compounds were identified from the primary screen (FIG. 2c and Table 2). As seen in FIG. 1, two of these compounds, UNC0638 and UNC0642, were validated and shown to be active in concentration responses (FIG. 1d) and quantitative reverse transcription PCR (RT-qPCR)(FIG. 1e). FIG. 1a represents screening strategy using a cell-based model. FIG. 1b represents high content imaging of Snrpn-EGFP following immunofluorescence staining by GFP antibody. Representative images of maternal Snrpn-EGFP MEFs are shown. FIG. 1c shows chemical structures of the identified hits. FIG. 1d shows concentration response curves of UNC0638, UNC0642, and UNC617 in maternal Snrpn-EGFP MEFs. FIG. 1e represents validation of Snrpn-EGFP mRNA expressions in G9a inhibitor- or 5-Aza-dC-treated MEFs using qRT-PCR (Livak methods, normalization to β-actin, p<0.05; t-test, n=3, three independent experiments).

Both UN0638 and UNC0642 have been characterized as G9a-selective inhibitors which bind to and block the G9a catalytic domain. Through an extended screening of 23 additional analogues of UNC0638 and UNC0642, two additional compounds that also activated the expression of S-EGFP in $m^{S-EGFP}/p^+$ MEFs were identified: UNC617 and UNC618 (FIG. 1c). UNC0638, UNC0642, and UNC617 displayed similar potency as shown by the concentration response curves (FIG. 1d, half-maximal effective concentration ($EC_{50}$)=1.6 µM for UNC0638; 2.7 µM for UNC0642; and 2.1 µM for UNC617). The estimated maximal effectiveness ($E_{max}$) was similar for these three compounds whereas UNC618 was only effective at 30 µM. Next, qRT-PCR was performed to measure the changes in mRNA of S-EGFP. These compounds upregulated the mRNA of S-EGPF to an extent comparable to or greater than 5-aza deoxycytidine (5-Aza-dC), an inhibitor of DNA methyltransferases (DNMTs) (FIG. 1e). Because other allele-specific histone modifications, such as acetylation, occur in the PWS-IC, it was determined whether the modulation of other classes of histone modifying enzymes could activate S-EGFP. However, it was found that histone deacetylase (HDAC) inhibitors such as trichostatin A (TSA), vorinostat (suberoylanilide hydroxamic acid: SAHA), entinostat (MS-275), and valproic acid as well as S-adenosyl-methionine and sinefungin, the cofactor and a broad inhibitor of histone methyltransferases, did not have an effect on activation of S-EGFP (Table 3). Interestingly, BIX01294, the first reported G9a inhibitor, which is less potent than UNC0638 and UNC0642, did not have a substantial effect on activation of S-EGFP (Table 3). These data illustrate that the activating effects of the compounds identified herein are relatively specific and probably result from targeting specific histone methyltransferases.

Example 2

Figure 3:
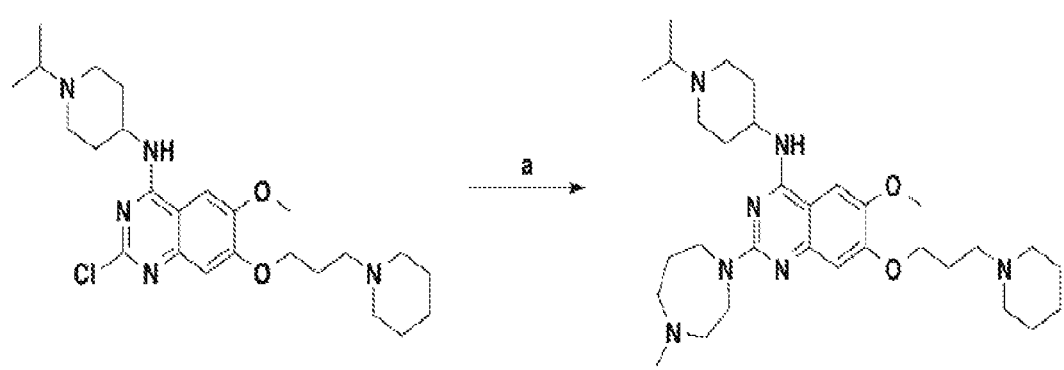
FIG. 3. Summarized data plot and positive active compounds from HCS. (a) Validation of HCS screening results. (b) Summarized data plot with all 9,157 compounds, including constitutively active paternal Snrpn-EGFP as positive control (c) 32 potential compounds activating Snrpn-EGPF at over 125%.

Synthesis of Compound which Activates the Expression of S-EGFP in $m^{S-EGFP}/p^+$ MEFs N-(1-isopropylpiperidin-4-yl)-6-mehtoxy-2-(4-methyl-1,4-diazepan-1-yl)-7-(3-(piperidin-1-yl)propoxy) quinazolin-4-amine, named UNC617, was synthesized as follows and as represented in FIG. 3. A mixture of compound 1 (70 mg, 0.15 mmol), 1-methyl homopiperazine (34 mg, 0.30 mmol), and TFA (46 µL, 0.60 mmol) in i-PrOH (0.2 mL) in a sealed tube was heated by microwave irradiation to 160° C. for 15 min. After concentration in vacuo, the crude product was purified by preparative HPLC with a gradient from 10% of MeOH in 0.1% TFA in H2O to 100% MeOH. The resulting product was basified with saturated aq. NaHCO3 and extracted with CH2Cl2 to afford the title compound as a yellow solid (60 mg, 0.11 mmol, 72% yield). 1H NMR (400 MHz, CDCl3) δ 6.87 (s, 1H), 6.72 (s, 1H), 5.00 (d, J=8.0 Hz, 1H), 4.11(t, J=6.0 Hz, 2H), 4.05-4.01 (m, 1H), 3.96-3.94 (m, 2H), 3.87-3.83 (m, 5H), 2.89 (app. d, J=12.0 Hz, 2H), 2.77-2.70 (m, 1H), 2.69-2.66 (m, 2H), 2.56-2.53 (m, 2H), 2.43 (t, J=8.0 Hz, 2H), 2.38-2.26 (m, 9H) 2.15 (app. d, J=12.0 Hz 2H), 2.06-1.95 (m, 4H), 1.60-1.50 (m, 6H), 1.42-1.39 (m, 2H), 1.05 (d, J=4.0 Hz, 6H). 13C HNMR (100 MHz, CDC13, 5 overlapping peaks) δ 158.5, 157.9, 153.9, 149.6, 145.1, 106.9, 102.6, 101.5, 67.3, 58.9, 57.3, 56.6, 55.7, 54.5(2C), 54.4(2C), 48.6, 47.7, 46.7, 45.8, 45.8, 32.5, 27.8, 26.4(2C), 25.9(2C), 24.4, 18.4(2C). HPLC: 98%; tR 0.56 min. HRMS (TOF) calculated for C31H52N7O2 [M+H]+, 554.4177; found 554.4192.

Synthesis of UNC0638, UNC0642, and their analogs can be seen in previous publications, Vedadi, M., et al., *Nat. Chem. Biol.* 7, 566-574 (2011); Liu, F. et al., *J. Med. Chem.* 56, 8931-8942 (2013); Liu, F. et al., *J. Med. Chem.* 54, 6139-6150 (2011); Liu, F. et al., *J. Med. Chem.* 52, 7950-7953 (2009); and Liu, F. et al., *J Med Chem* 53, 5844-5857 (2010), all of which are incorporated herein by reference in their entirety.

Example 3

Examining Effects of Unsilencing Molecules in a PWS Patient Driven Cell Model

Figure 4:
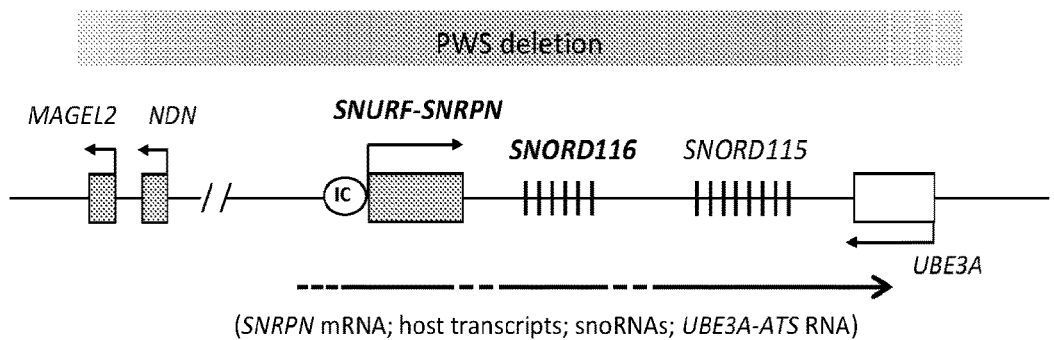
FIG. 4. Effects of UNC0638 on unsilencing of candidate PWS genes in a human PWS cell model. (a) Schematic of genomic organization at the human chromosome 15q11q13 region IC, imprinting center. (b) Schematic of in vitro treatment used in (c-e). (c) RT-PCR (left) and concentration-response curves (right) of SNRPN and SNORD116 in UNC0638-treated human fibroblasts (PWS, cell line derived from a PWS patient; ctrl, from a non-PWS individual; M, 1 kb DNA ladder). (d) Western blot and quantification of SNRPN protein in human PWS fibroblasts with or without UNC0638 treatment (4 μM for 72 hr). (e) RT-PCR analysis of genes and transcripts from 15q11-q13 in human PWS fibroblasts treated with UNC0638, UNC0642, UNC617, UNC618, or 5-Aza-dC.
Figure 4:
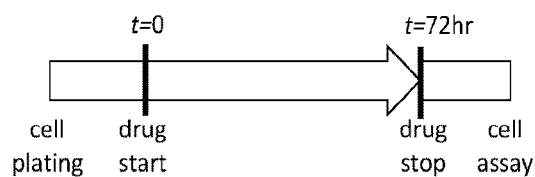
Figure 4:
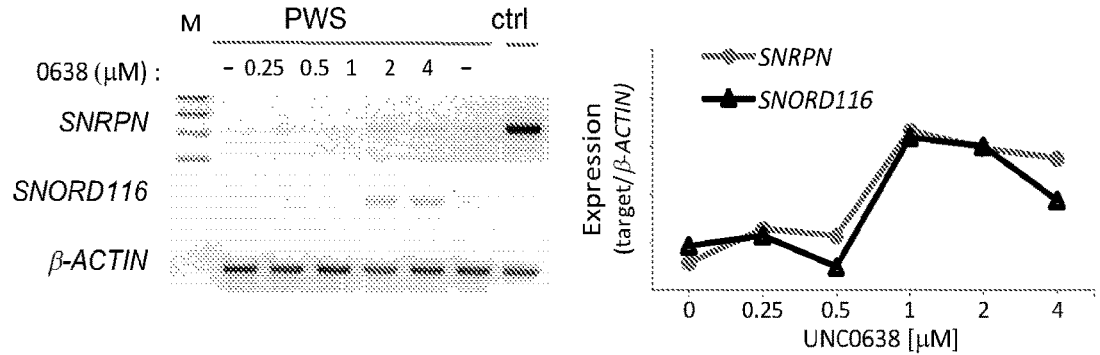
Figure 4:
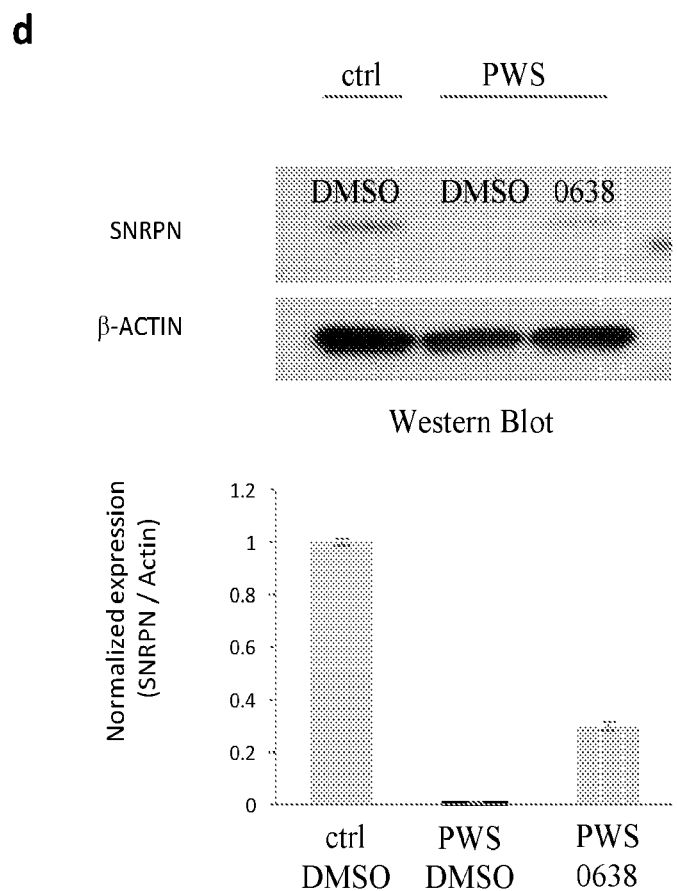
Figure 4:
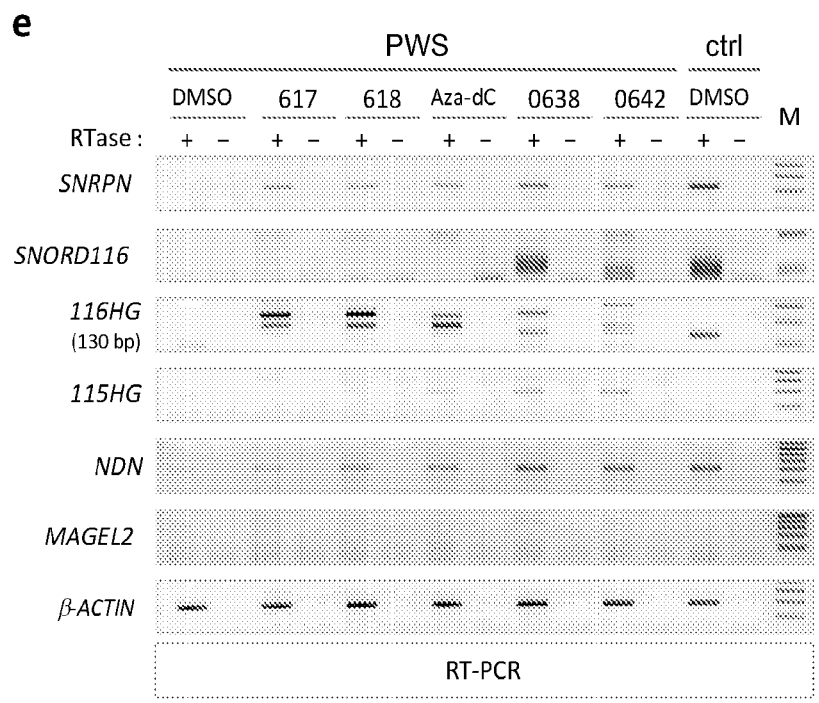

A skin fibroblast cell line containing a typical large (5-6 Mb) deletion of the paternal copy of the 15q11-q13 region was used to determine if UNC0638 and UNC0642 could depress the maternal genes in a patient-driven cell model of PWS. FIG. 4a represents a schematic of genomic organization at the human chromosome 15q11-q13 region imprinting center. Because imprinting of SNPRN is known to be ubiquitous, the G9a-inhibitor effect on its activation is expected to be representative of all tissues and cell types.

Figure 5:
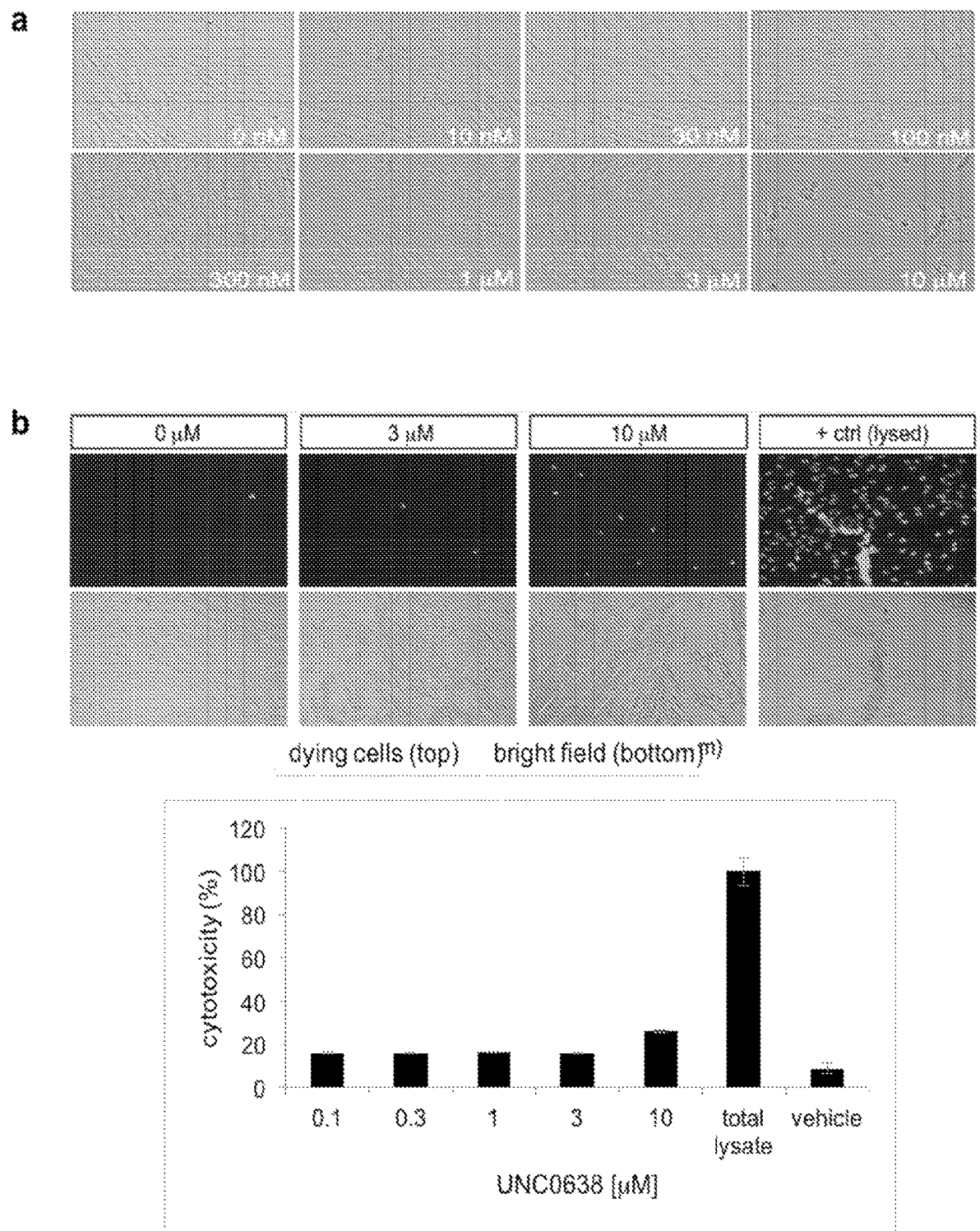
FIG. 5. Evaluation of drug toxicity. (a) The brightfield images of human PWS fibroblast cells treated with UNC0638 for 72 hours are shown to provide gross cell morphology at various dosage increments. (b) Quantification of cytotoxicity.

For cell-based studies as represented in FIG. 4b, UNC0638 was chosen due to its high potency and selectivity, low toxicity, and thoroughly characterized cellular activity. UNC0638 treatment (1-4 µM) effectively activated SNRPN and SNORD116 transcripts, as assessed by RT-PCR (FIG. 4c) with a minimal cytotoxicity (FIG. 5). PWS fibroblasts treated with 4 µM UNC0638 expressed approximately 30% of normal SNRPN protein levels as shown by Western blot in FIG. 4d. Additional genes regulated by the PWS-IC, including SNRPN, host transcripts of SNORD116 (HG116) and SNORD115 (HG115), and NDN were further examined. FIG. 4e shows RT-PCR analysis of genes and transcripts from 15q11-q13 in human PWS fibroblasts treated with UNC617, UNC618, UNC0638, UNC0642, or 5-Aza-dC (ctrl, control; HG116, host transcript for SNORD116; HG115, host transcript of SNORD115; RTase: +/−, with/without reverse transcriptase). The effectiveness of four identified compounds and 5-Aza-dC as a control were compared. All showed activating effects on the SNRPN mRNA expression. However, only UNC0638 and UNC0642 were effective for SNORD116, and its putative host transcript (116HG). While a single PCR product for 116HG was detected in the control, multiple bands were seen in the drug treated cells. These products were verified by sequencing analysis and were mapped to the region of the host transcripts for SNORD116. The additional host transcripts in the drug-treated cells may suggest the activation of cryptic splicing or the promoter by drug treatment for the host transcripts. Drug treatments also reactivated the expression of NDN that is 1 Mb proximal to PWS-IC. MAGEL2 activation was unable to be determined because MAGEL2 is not normally expressed in skin fibroblasts. Taken together, these expression analyses strongly indicate that UNC0638 and UNC0642 are capable of unsilencing the maternal copy of paternal expressed genes from the PWS region in cells derived from both mice and humans.

Example 4

Examining the Effects of Unsilencing Compounds In Vivo

Figure 6:
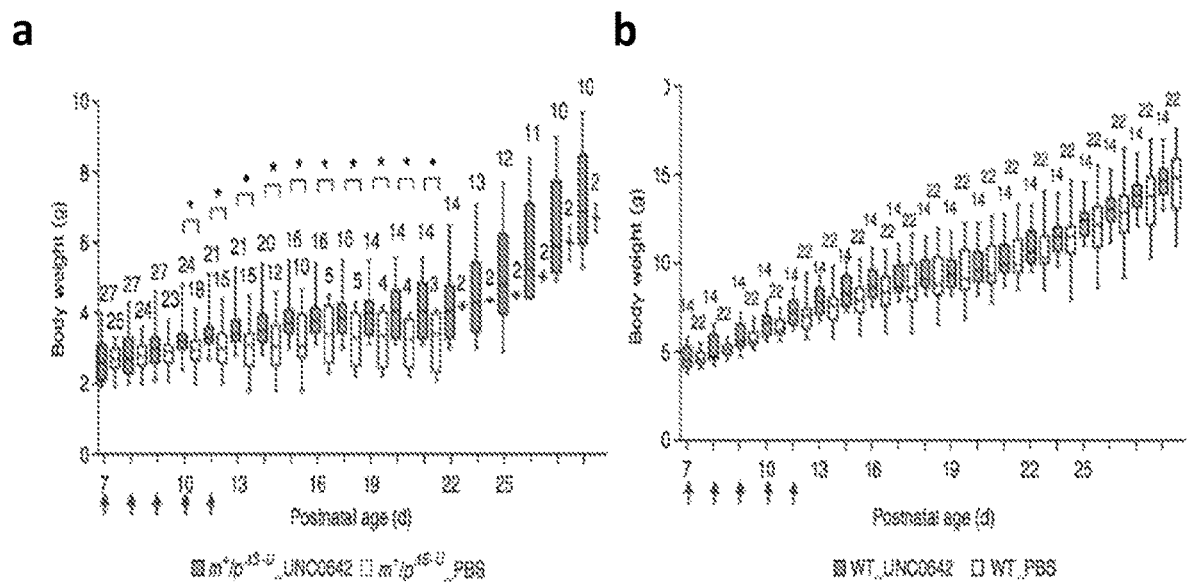
FIG. 6. Representation of UNC0642 improves survival and growth in mouse model with paternal deletion from Snrpn to Ube3a ($m^+/p^{\Delta S\text{-}U}$). (a) Changes in weight gain in m+/p S-U mice with or without the treatment of UNC0642. Box-and-whisker plots correspond to body weight of PBS-treated m+/p S-U (open blue, n=25 mice at P7 and n=2 mice at P25); UNC0642-treated m+/p S-U (blue, n=27 mice at P7 and n=6 mice at P25) (Student's t test; *P<0.05; between two groups of PWS_UNC0642 and PWS_PBS from P10 to P19). (b) Changes in weight gain in WT mice with or without the treatment of UNC0642 (open black line, n=22 mice at P7 and n=22 mice at P25); treated WT (black, n=14 mice at P7 and n=14 mice at P25). Two-way ANOVA; treatment; P<0.0001; F=863.3, genotype; P<0.0001; F=14.86, interaction; P<0.0001; F=2.86 from P10 to P19; data are means with max and min.

Using a mouse PWS model which carries a paternal deletion from Snrpn to Ube3a ($m^+/p^{\Delta S-U}$), the effects of UNC0642 in vivo were examined. UNC0642 was chosen due to the qualities of it not only having a high potency and selectivity for G9a in biochemical and cellular assays, but also pharmacokinetic (PK) properties including CNS penetration superior to UNC0638. A single dose of 5 mg/kg intraperitoneal (i.p.) injection of UNC0642 is sufficient to inhibit G9a activity in adult mice. The m/p$^{\Delta S-U}$ pups were treated between postnatal day 7 (P7) and P12, as most m+/p$^{\Delta S-U}$ pups died before weaning. For neonatal PWS mice, a lower dose regimen of 2.5 mg/kg i.p. injections for 5 consecutive days was used. FIG. 6a shows a schematic of in vivo treatment of m+/p$^{\Delta S-U}$ mice. Pups at postnatal day 7 (P7) were treated with a daily dose of 2.5 mg/kg for 5 days. As shown in FIG. 6b, the UNC0642 treatment was well tolerated in both wild type and the m/p$^{\Delta S-U}$ pups and significantly attenuated lethality of PWS mice as compared to the untreated control group (Kaplan-Meier Log rank test, p=0.0086). The difference in the survival rates of PWS pups was most notable during the first week after drug administration and diminished over time. Six UNC0642-treated m+/p S-U pups survived to >P90 (15%; n=40), and they had normal physical appearance and activity in their home cages. Body-weight measurements revealed that there was a significant improvement of growth between P10 and P19 in treated m+/p S-U pups (FIG. 6a). These results indicate the partial rescue of lethality and growth-delay phenotypes of the PWS mouse model, and hence the potential of such treatment for humans.

Figure 7:
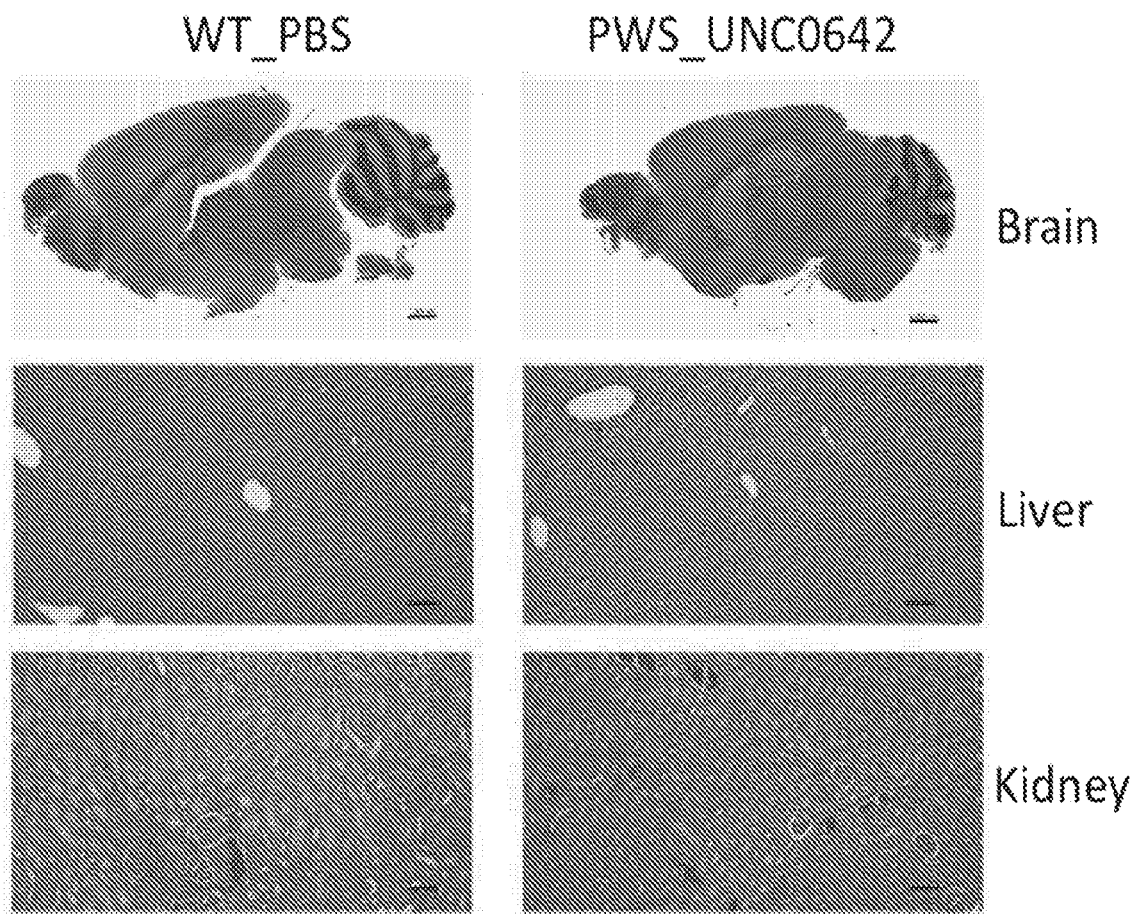
FIG. 7. Photomicrographs of UNC0642-treated PWS and vehicle-treated WT animals at age of 3 months. Hematoxylin and eosin stained sagittal sections of brain (scale bar, 1000 μm), liver and kidney (scale bar, 1000 μm). Histopathologic examination revealed no significant compound related lesions in any of the tissues examined (lung and heart, not shown).

To assess the potential toxicity associated with UNC0642 treatment, we monitored body weight in WT groups. Notably, loss of body weight, a sign of general health deficiency, was not observed in WT mice treated with UNC0642 (FIG. 6b). We also performed a general health and neurological screening in a blinded fashion, and it did not reveal any substantial abnormalities (Table 6). In additional toxicity tests, we did not include vehicle-treated PWS mice because of the small sample size. Despite our breeding effort that produced a total number of 60 m+/p S U pups, only two vehicle-treated m+/p S U mice survived to P90. In hematological analysis, the measurements of treated m+/p S-U and WT mice were within normal ranges, as measured by liver and kidney functions as well as normal lipid and protein metabolism, which are indicative of normal health conditions (Table 7). Histopathological analyses also did not reveal any abnormalities associated with UNC0642 treatment in the brain, liver, kidney, lung and heart from mice at P90, both in m+/p S U and WT mice (FIG. 7).

Figure 8:
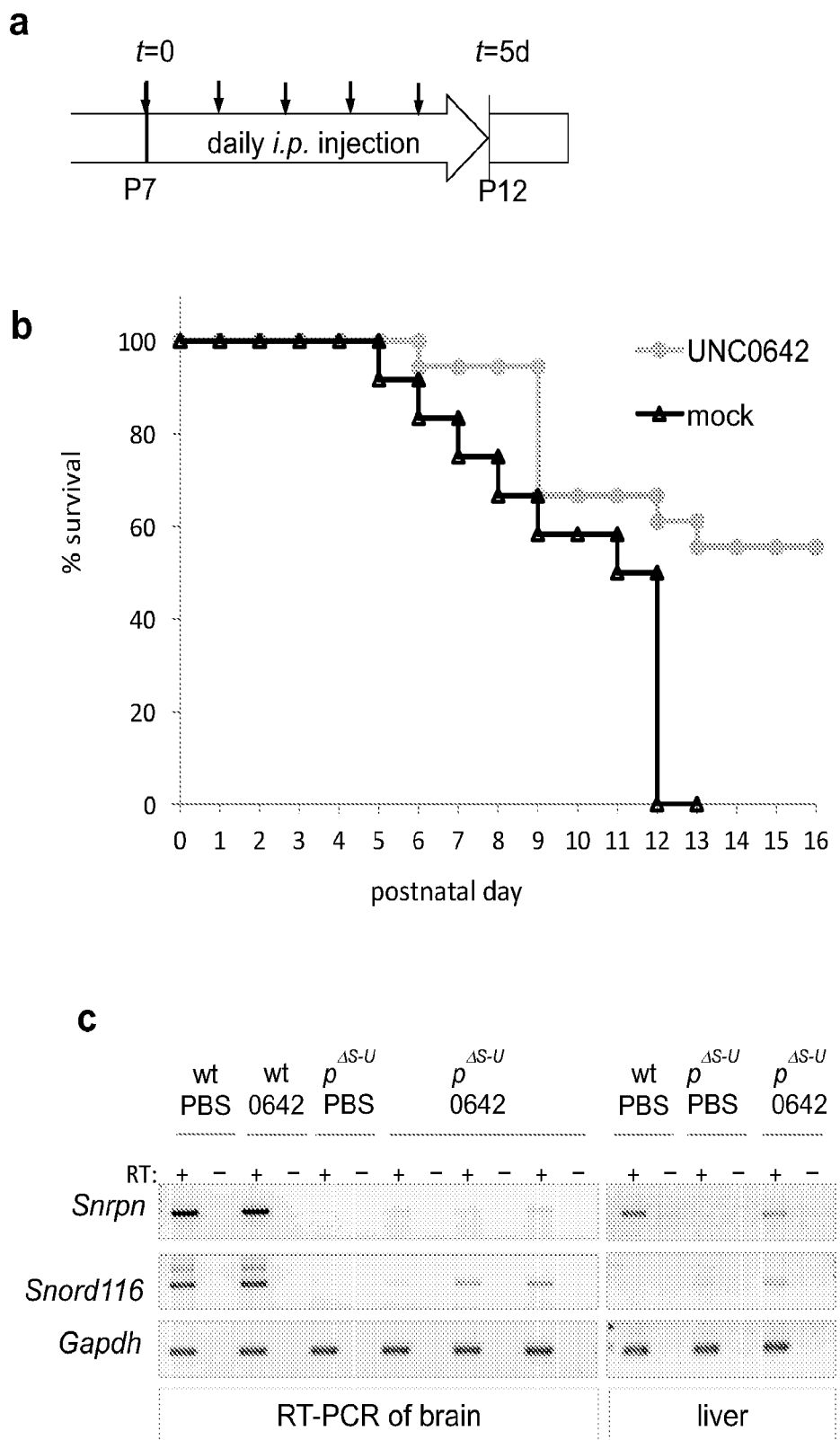
FIG. 8. UNC0642 improves survivability and unsilences candidate PWS genes in mouse models with a paternal deletion from Snrpn to Ube3a ($m^-/p^{\Delta S\text{-}U}$). (a)) Schematic of in vivo treatment of $m^+/p^{\Delta S\text{-}U}$ mice. (b) Improved survival of UNC0642-treated PWS pups (Kaplan-Meier Log rank test, p=0.0086; $X^2$=6.9041; df=1). (c) and (d) Expression analysis of Snrpn, Snord116, host transcript 116HG, and Ube3a-AS by conventional RT-PCR (c) and qRT-PCR (d) of brain and liver from P15-16 $m^+/p^{\Delta S\text{-}U}$ pups with or without treatment. (e) Western blot and quantification of Ube3a and Snrpn proteins in brain. (f) Schematic of treatment in 6 week-old mice. The expression of Egfp by RT-PCR (g) and qRT-PCR (h) in brain demonstrates efficacy of treatment and long-term effects in adult mice.
Figure 8:
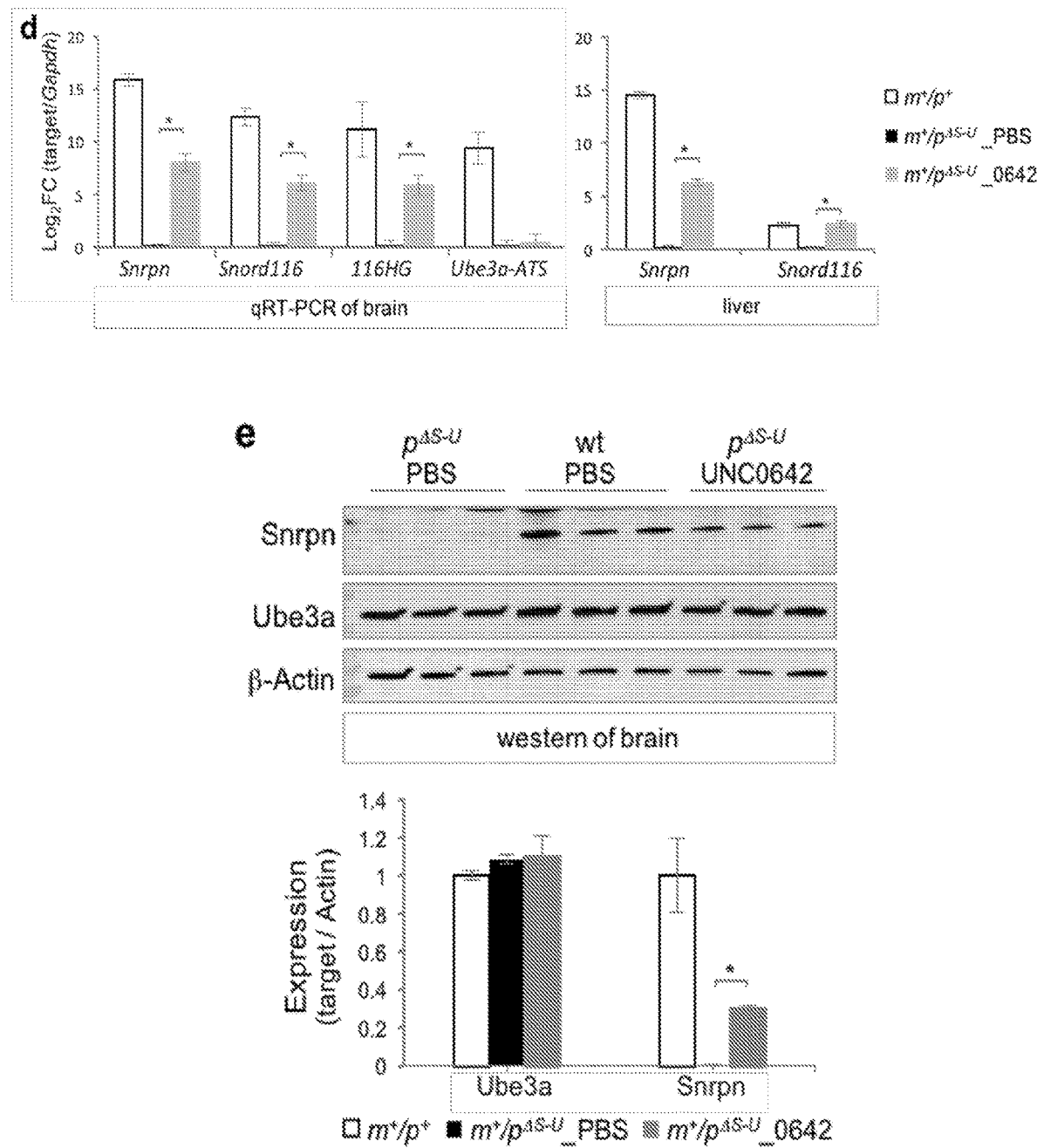
Figure 8:
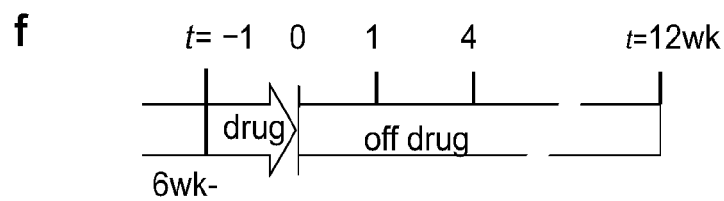
Figure 8:
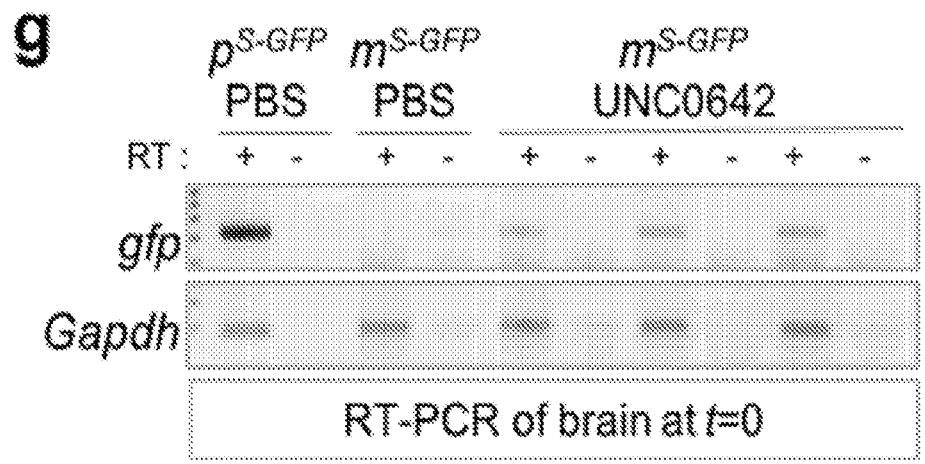
Figure 8:
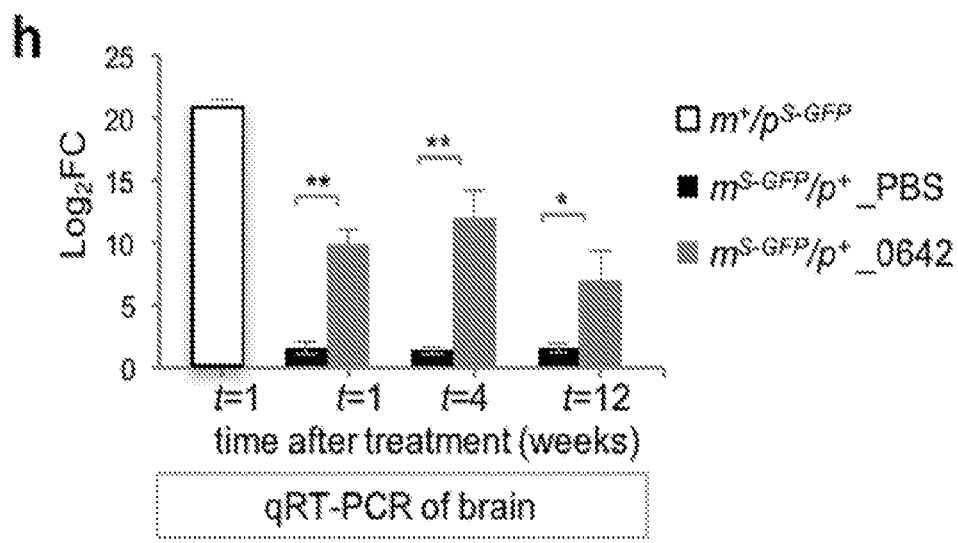
Figure 9:
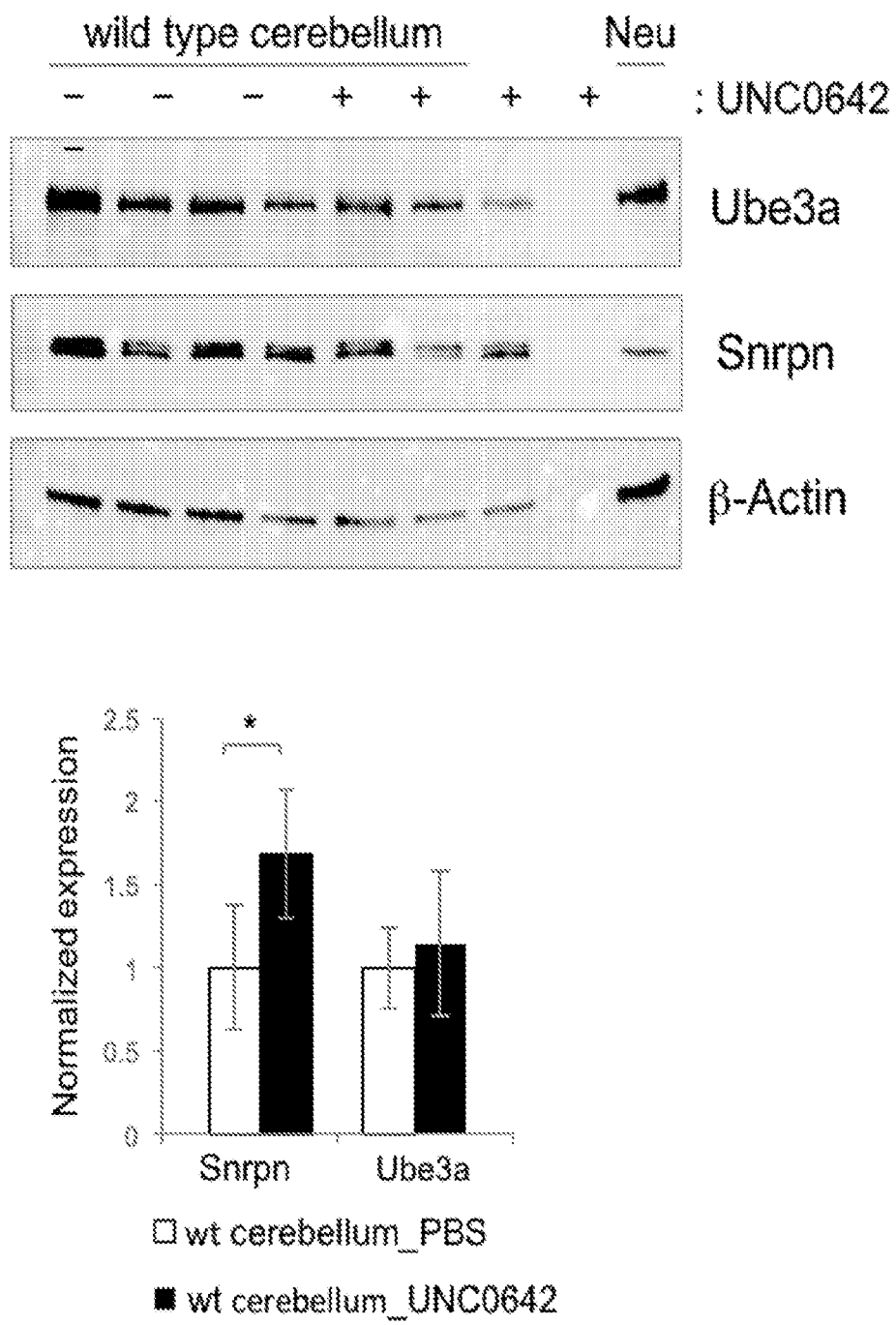
FIG. 9. Angelman syndrome UBE3A expression was not affected by UNC0642. Normalized protein levels of UBE3A and SNPRN in cerebellum following in vivo treatment with PBS (−) or UNC0642 (+, 5 mg/kg, three daily i.p. injections). The lane marked neu, represents cultured primary cortical neurons, and was included as internal control (*p<0.05; t-test; n=3-4 mice per group).

RNA and protein expression was assessed in m+/p$^{\Delta S-U}$ mice at around P14 following the treatment (FIG. 8a, c-e). Whereas the expression of Snrpn and Snord116 was readily detectable in the brain and liver of UNC0642 treated m+/p$^{\Delta S-U}$ mice, PBS treated m+/p$^{\Delta S-U}$ mice had no detectable transcripts as shown by conventional and quantitative RT-PCR as represented in FIGS. 8c and 8d, respectfully. The effect of this activation on the maternal expression of Ube3a was determined because the Ube3a antisense transcript (Ube3a-AS) is essential in silencing the paternal copy of Ube3a in the brain and is only expressed paternally. Importantly, FIG. 8d shows that the level of Ubea3-AS RNA was not affected in the brain. Similarly, FIG. 8e shows the Ube3a protein level was not changed in the whole brain or specifically in the cerebellum where the maternal-specific Ube3A transcript is predominantly expressed (FIG. 9). The unsilencing effect of UNC0642 was confirmed in an adult Snrpn-EGFP mouse model (FIG. 5). Treatment with UNC0642 exerted a long lasting effect as shown by the maternal expression of Snrpn-EGFP at 1, 4, and 12 weeks after the last dose of UNC0642 by conventional RT-PCR (FIG. 8g) and qRT-PCR (FIG. 8h). However, it is worth noting that the level of expression at 12 weeks was significantly lower than that at 4 weeks (p=0.03). These results demonstrate the in vivo efficacy of the UNC0642 in a PWS mouse model and provide sufficient proof-of-principle to evaluate therapeutic intervention targeted at the molecular etiology of PWS.

Example 5

Figure 10:
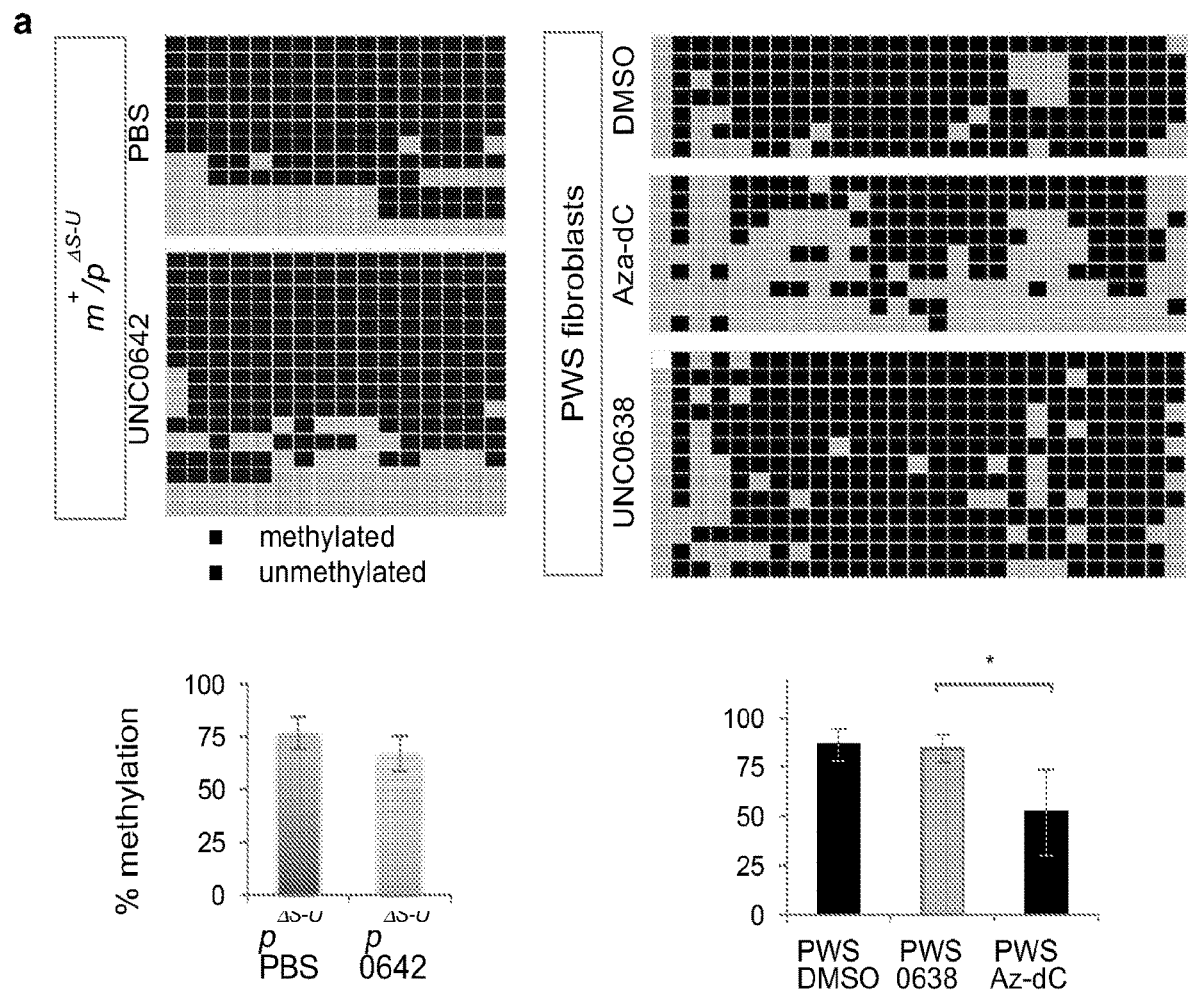
FIG. 10. Unsilencing of PWS candidate genes by UNC0638 and UNC0642 is associated with demethylation of H3K9 and enhanced chromatin accessibility. (a) Comparison of the DNA methylation in PWS-IC between vehicle- and UNC0642 or UNC0638 treated in liver of $m^+/p^{\Delta s-u}$ mice and in a human PWS fibroblast cell lines. (b) Genomic DNA PCR following chromatin immunoprecipitation of H3K9me2 or H3K9me3 in PWS fibroblasts. (c) ChIP-qPCR quantification of H3K9me2 and H3K9me3. (d) Increased chromatin accessibility in the PWS imprinted domain by UNC0638. (e) Schematic of the histone mechanism for maternal unsilencing of the PWS region.
Figure 10:
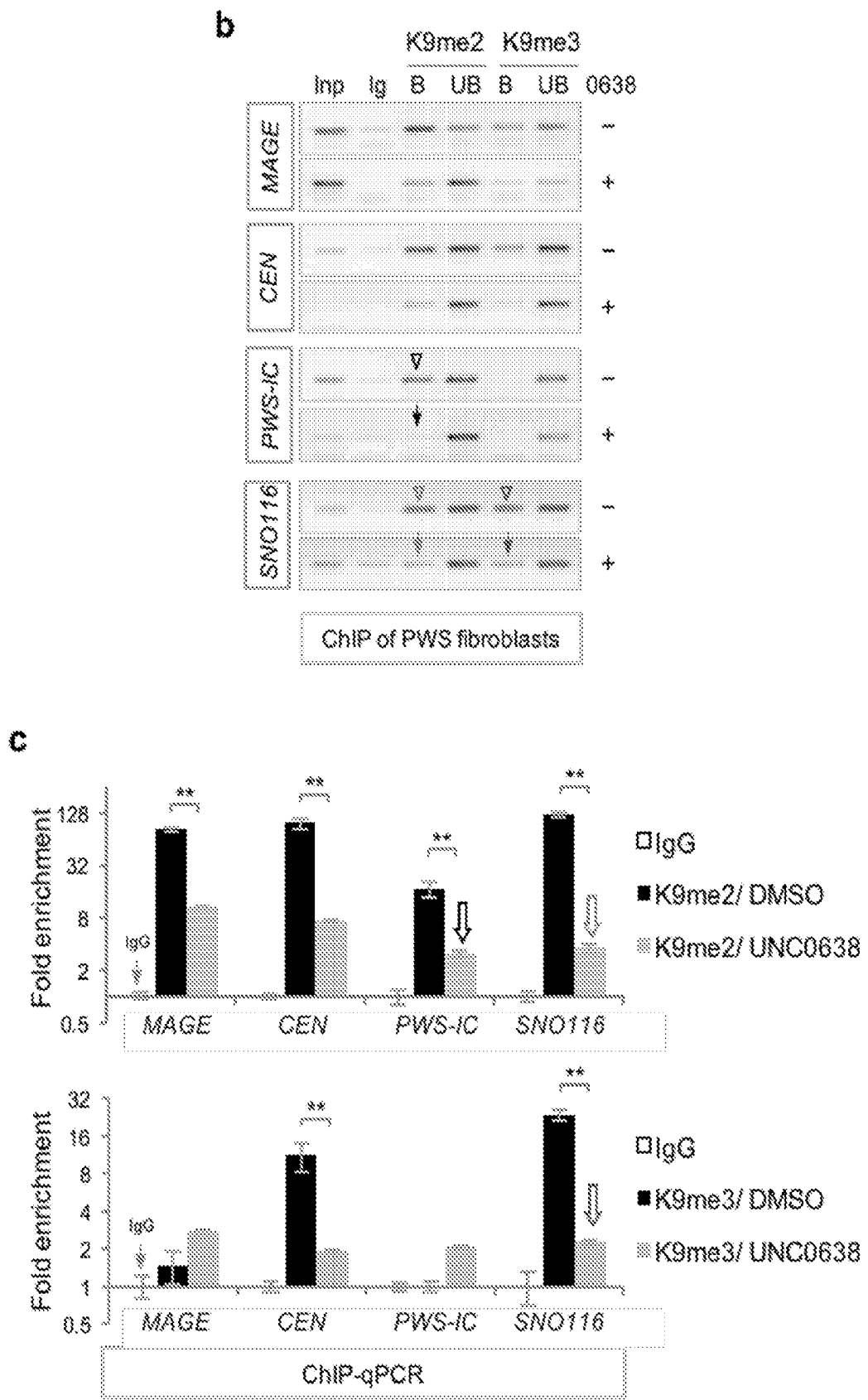
Figure 10:
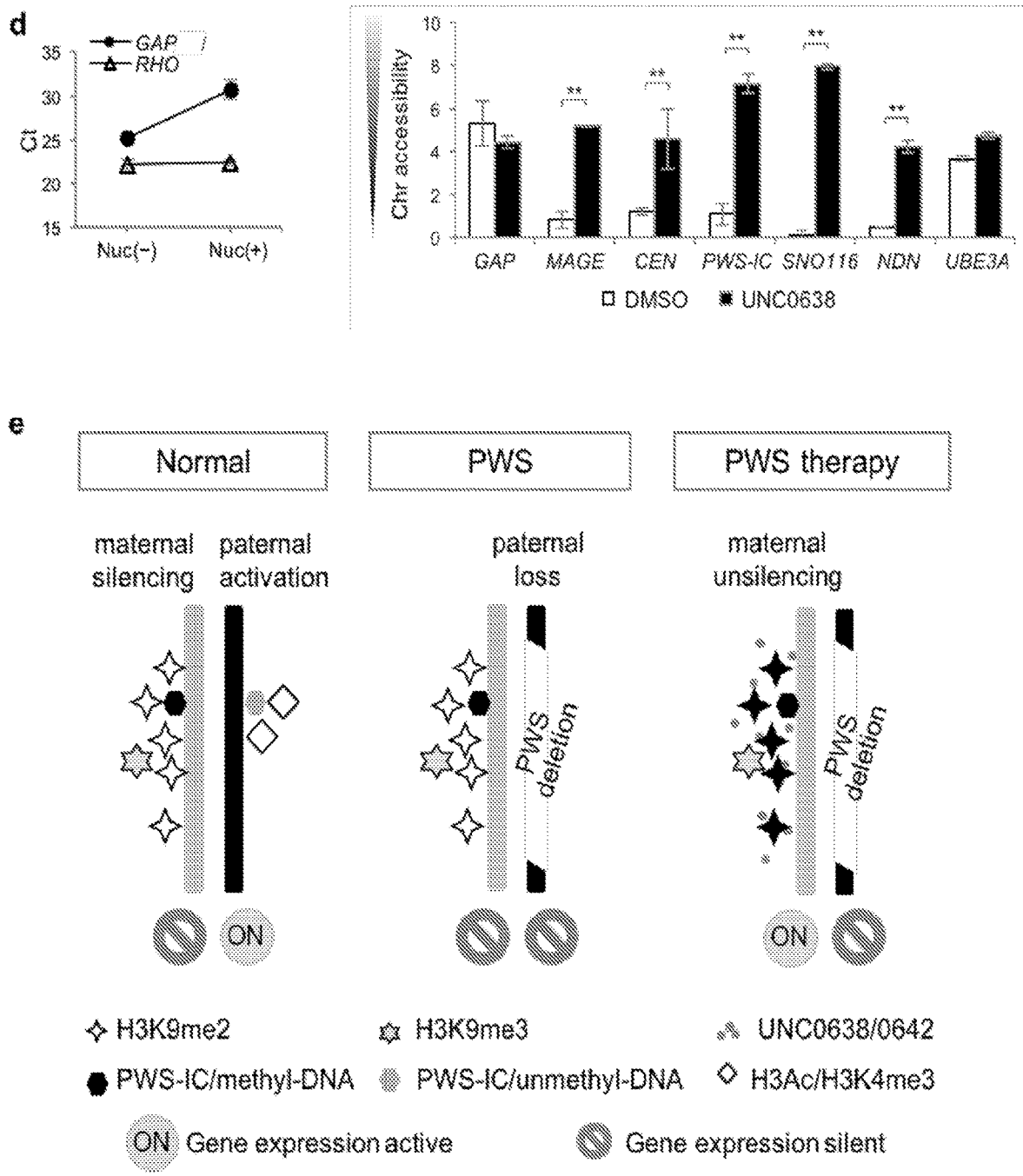

Determining Mechanistic Association of Pharmacological Inhibition of G9a by Unsilenceing Compounds The underlying mechanism for the unsilencing of the maternal chromosome 15q11-q13 by UNC0638 and UNC0642 was investigated to examine whether the activation of PWS genes is directly associated with pharmacological inhibition of G9a by these compounds. The allele-specific methylation of the PWS-IC is thought to implicate the imprinted regulation of candidate PWS-associated genes. G9a is also known to have capacity to modulate DNA methylation. Although it has been shown that UNC0638 does not significantly alter the global DNA methylation, concentration-dependent hypomethylation of long terminal repeats (LTR) for individual genomic loci was observed in cells treated with UNC0638. It was first examined whether the DNA methylation of the PWS-IC was affected in liver tissues from m+/p$^{\Delta S-U}$ mice and human PWS cells treated with UNC0642 and UNC0638, respectively. As a positive control, it was confirmed that 5-Aza-dC significantly decreased DNA methylation of the PWS-IC. In contrast, UNC0638 and UNC0642 did not significantly alter DNA methylation of the PWS-IC either in human PWS cells or in livers from PWS mouse models. As FIG. 10a shows, the square plot illustrates the methylation pattern for individual CpG sites (filled square for the methylated and open square for the unmethylated CG site). The graph is the average methylation measured by the number of methylated CG sites divided by the total number of CG sites analyzed. (*p<0.05; t-test, n=7-13 per group).

Figure 11:
FIG. 11. Verification of ChIP assay in the PWS/AS cell lines.
Figure 12:
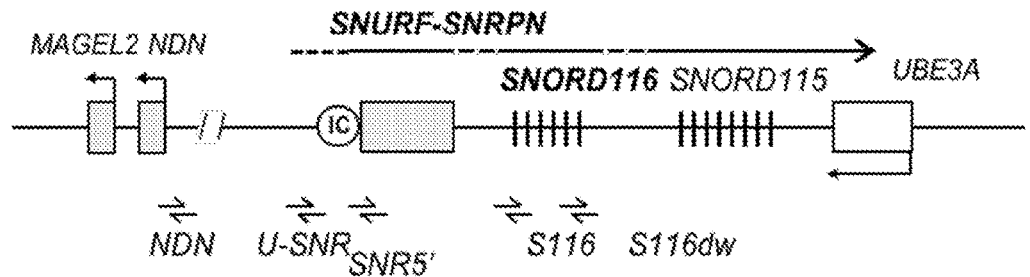
FIG. 12. Enrichment of H3K9me2 at different PWS candidate gene loci. (a) The positions of PCR primer pairs used for chromatin assays across the 15q11-q13 region including NDN (the promoter region of NDN); U-SNR (the region at the most upstream of untranslated exons of SNRPN; PWS-IC (the region overlap with the CpG island of SNRPN and PWS-IC); and S116dw (the 3' region of SNORD116 cluster). (b) ChIP-qPCR analysis of H3K9me2 in PWS imprinted domain.
Figure 12:
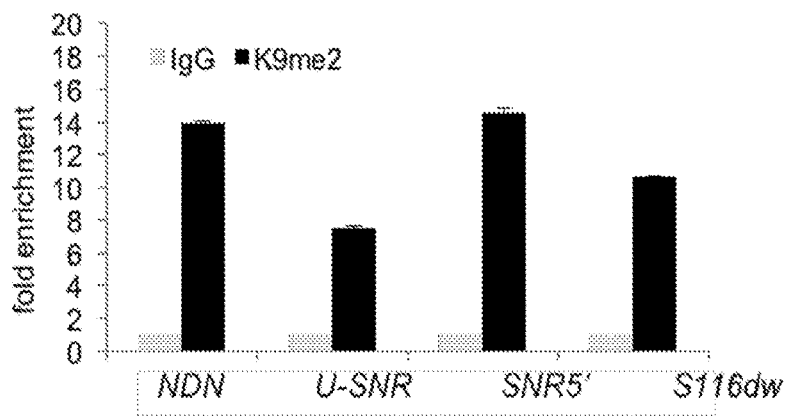
Figure 12:
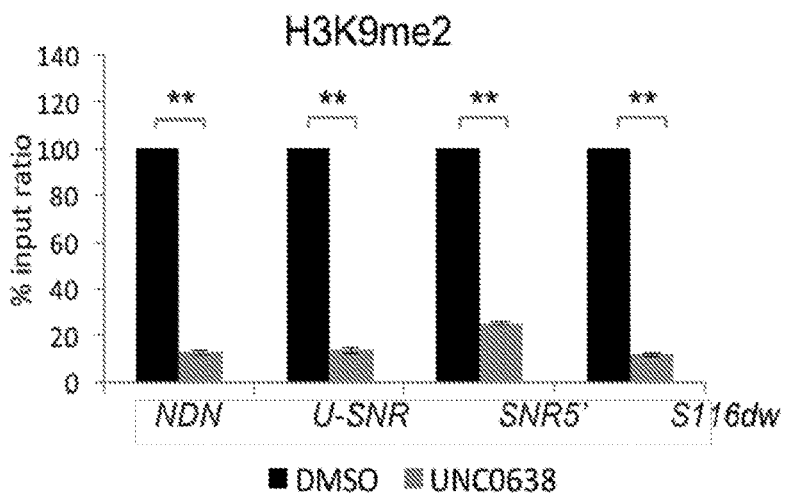

Next, chromatin immunoprecipitation (ChIP) assays were performed to examine whether the G9a-mediated methylation of H3K9 is affected. Both H3K9me2 (dimethylation of H3K9) and H3K9me3 (trimethylation of H3K9) are associated with gene silencing and facilitate the heterochromatin formation. FIG. 11 shows assay verification by confirming that H3K9me2 and H3ac (acetylation of H3) were enriched at the maternal or paternal PWS-IC, respectively. Using the MAGE A2 promoter (MAGE) and a centromere sequence (CEN) as controls, UNC0638 drastically reduced the level of H3K9me2 and H3K9me3 in the PWS-IC and SNORD116 regions (FIGS. 10b and c). Importantly, H3K9me2 enriched at the PWS-IC was significantly reduced in the UNC0638-treated cells compared to the untreated (empty black arrowhead and black arrow in FIG. 10b; empty black block arrow in FIG. 10c; reduction of 17-fold to 3-fold, p<0.05). The treatment of 5-Aza-dC also reduced H3K9me2 in the PWS-IC of the maternal chromosome in cultured cells (FIG. 11). As seen in FIG. 12b, UNC0638 also reduced H3K9me2 in the region associated with NDN. At the region of the host transcript of SNORD116, both H3K9me2 and H3K9me3 were enriched (FIG. 10b open arrowheads in the upper panel of SNO116) and UNC0638 treatment reduced both H3K9me2 and H3K9me3 as compared to untreated controls (FIG. 10c H3K9me2: reduction of 122-fold to 4-fold, p<0.05; and H3K9me3: reduction of 24-fold to 2-fold, p <0.05).

Figure 13:
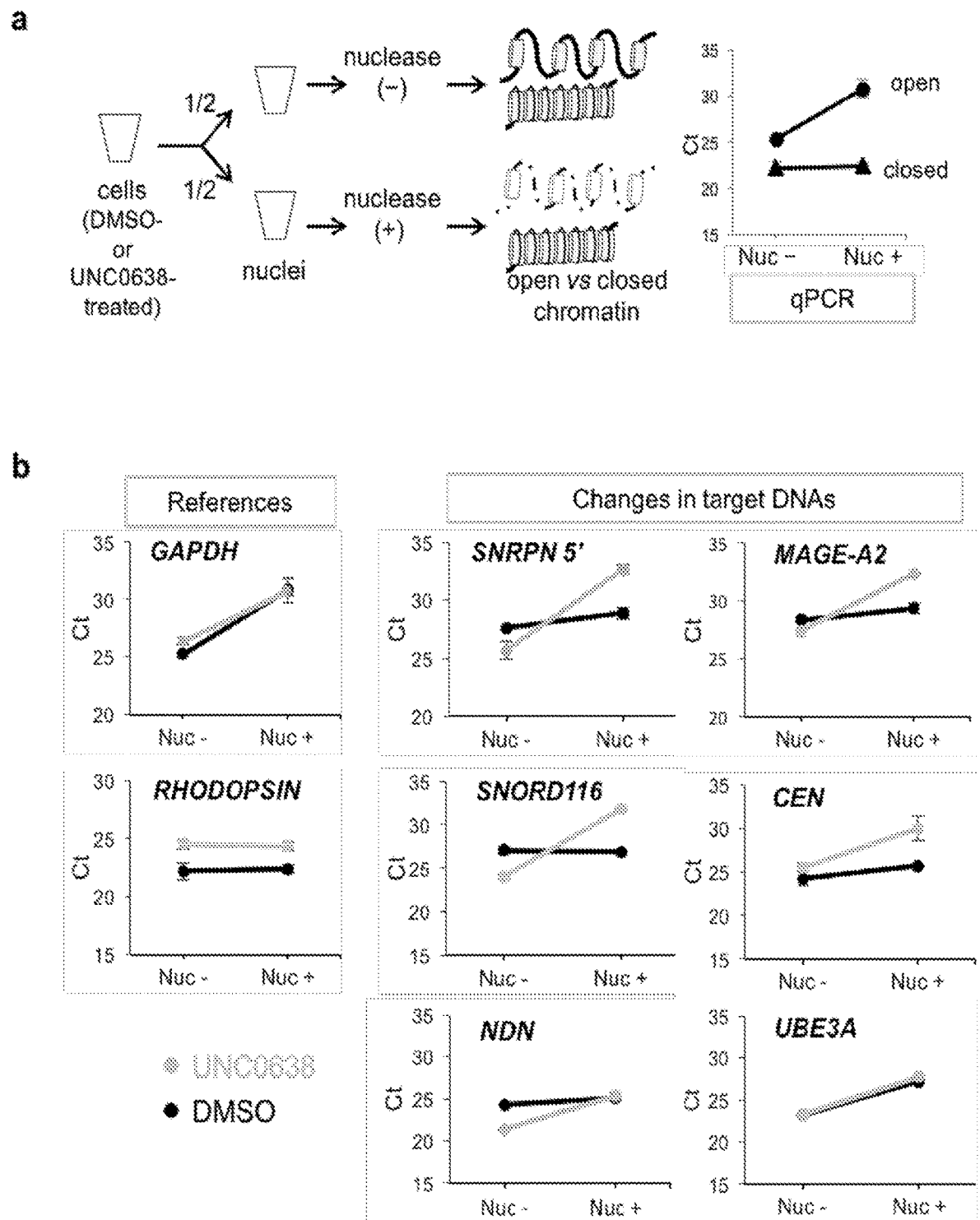
FIG. 13. Chromatin state at the silent maternal PWS region is H3K9me2-dependent. (a) Schematic diagram of chromatin accessibility assay along with qPCR was used to determine the amount of indicated DNA. (b) The chromatin accessibility of genomic loci across PWS region assessed by genomic qPCR.

H3K9me2 facilitates heterochromatin formation to regulate transcription; therefore, it was determined whether the reduction of H3K9 methylation could result in more open chromatin across the imprinted domain. Quantitative PCR (qPCR) of genomic DNA following in situ nuclease digestion was performed to measure chromatin accessibility (FIG. 10d and FIG. 13a) using the protocol as previously described in Pai et al Nature communications 5, 4091 (2014). The following controls were used in this study: the constitutively expressed GAPDH (GAP) which was highly susceptible to nuclease digestion, and constitutively silent RHODOPSIN (RHO) which displayed minimal chromatin accessibility, regardless of the UNC0638 treatment (FIG. 13b). As a result of the treatment with UNC0638, the target regions across the imprinted domains, including the SNRPN and SNORD116, were more open and accessible than vehicle-treated controls (FIG. 10d). The effect of UNC0638 and UNC0642 seemed to be bidirectional in reference to the PWS-IC in the PWS domain. These results suggest that the reduction of H3K9 methylation, but not DNA demethylation of PWS-IC, by the UNC0638 and UNC0642 treatment leads to more open chromatin, which, in turn, activates candidate PWS-associated genes from the maternal chromosome. FIG. 10e represents a schematic of the histone mechanism for maternal unsilencing of the PWS region where the modulation of H3K9me2 deposited on the maternally inherited PWS region is the basis to develop potential treatments for PWS. The pharmacological inhibition of G9a leads to the loss of H3K9me2 and hence changes chromatin to permissive states for the activation of the PWS genes.

The G9a inhibitors UNC0642 and UNC0638 identified from a HCS activate the candidate PWS-associated genes from the maternal chromosome both in human PWS patient-derived cells and in a PWS mouse model. Treatment with UNC0642 afforded a clear therapeutic benefit for PWS-related phenotypes, including perinatal lethality and poor growth, which resemble the common clinical features of failure to thrive in individuals with PWS during the first year of life. Further studies will determine whether G9a inhibitors might offer therapeutic benefit to other major clinical problems of PWS, such as obesity, hyperphagia and behavioral impairment, that occur in childhood or later, when appropriate animal models of PWS become available.

UNC0642 treatment does not affect the expression of Ube3a, a maternally expressed gene whose loss causes Angelman syndrome (AS). The activation of PWS-associated genes on the maternal chromosome raises a concern because it may activate Ube3a antisense RNA (Ube3a-ATS), which normally represses paternal Ube3a expression but is not expressed from the maternal chromosome. It is unclear how the derepression of the PWS-associated genes Snrpn and Snord116 occurs without affecting the expression of Ube3a-ATS. The generation and the processing of host transcripts from the interval between PWS-IC and Ube3a are not well understood. In contrast to the current notion of a long transcript IC-SNURF-SNRPN, we speculate that the expressions of Snord116 host transcript and Ube3a-ATS are regulated differently. A recent study in human tissues from healthy individuals found potential transcription start sites (TSSs) within the interval between PWS-IC and UBE3A (see Galiveti, C. R., et al., Sci. Rep. 4, 6445 (2014)): one between SNORD116 and SNORD115 clusters and another between SNORD115 and the 3 end of UBE3A. The large host transcript from the PWS-IC, which overlaps with the SNRPN promoter, might stop before these additional TSSs, and UBE3A-ATS might be initiated from one of potential TSSs, probably the one close to the 3' end of UBE3A. It seems that the disclosed G9a-inhibitor treatment derepresses the PWS-IC overlapping with Snrpn promoter, but not the TSS of Ube3a-ATS on the maternal chromosome. The continuous distribution of H3K9me2 along the PWS domain does not extend to the distal region, which then makes the TSS of Ube3a-ATS not targetable by the G9a inhibitor. Another possibility is that the effect of the G9a inhibitor might become weaker at the farther end distal to the PWS-IC.

It is not well understood how the functions of histone methylation and DNA methylation are linked for the repression of the PWS-associated imprinting domain in vivo. A previous genetic study showed that the PWS-IC was demethylated in G9a-deficient embryonic stem (ES) cells, whereas it was not affected in G9a-deficient mouse embryos (Xin, Z. et al., J. Biol. Chem. 278, 14996-15000 (2003)). Unfortunately, the expressions of PWS-associated genes have not been examined specifically in G9a-deficient embryos (which died at E9.5), presumably owing to technical difficulties associated with determining their allele-specific expression in embryonic tissue. The present disclosure demonstrates that the repressed SNRPN and SNORD116 are activated by the pharmacological inhibition of G9a, and that the reactivation occurred without any alteration of DNA methylation (5-methylcytosine, 5mC) of the PWS-IC both in vitro and in vivo. It should be noted that the possibility of modifications other than 5mC in PWS-IC being affected by the G9a inhibitor cannot be ruled out because the bisulfite method used for our DNA-methylation analysis cannot distinguish between 5mC and 5-hydroxymethylcytosine (5hmC), or between cytocine (C) and 5-carboxycytosine (5CaC). Nevertheless, the finding provides novel insight into the regulation of imprinting, whereby H3K9 methylation has a decisive role in the repression of PWS-associated genes on the maternal chromosome.

Previous genome-wide chromatin profiling has revealed an organized chromatin H3K9me2 modification in the PWS imprinted domain. H3K9me2 is associated with the silent maternal chromosome and G9a inhibitors selectively reduced di- and tri-methylation of H3K9. Such reductions are likely to alter the chromatin state to become permissive for unsilencing PWS genes. These findings uncovered by the pharmacological approach are supported by a previous genetic study that Snrpn is unsilenced in G9a-deficienct embryonic stem (ES) cells. Distinct from G9a inhibitors, which did not change DNA methylation, the CpG sites of the PWS-IC in the maternal chromosome are demethylated in G9a null embryonic cells. G9a deficiency causes early embryonic lethality at E8.5 day in mice. Interestingly, the DNA methylation of CpG sites in the PWS-IC of G9a null embryos is comparable with that in wild-type and the expression of Snprn has not been examined, presumably due to technical difficulty to determine the allele-specific expression of Snrpn in mouse embryos. In significant contrast with previous reports that methylation of the PWS-IC is important for silencing the expression of PWS genes in the maternal chromosome (see Fulmer-Smentek et al., Human Molecular Genetics 10, 645-652 (2001); Saitoh et al., American Journal of Human Genetics 66, 1958-1962 (2000)), the findings presented in this disclosure show that H3K9 methylation plays a decisive role in silencing the PWS genes. In support of this conclusion, treatment with 5-Aza-dC reduced H3K9 methylation in addition to DNA methylation in the PWS-IC. These findings support an imprinting mechanism in which the imprinted expression of PWS genes is regulated by H3K9 methylation mediated chromatin accessibility (FIG. 11e).

In the present disclosure, the G9a inhibitor UNC0642 is shown to improve the survival of $m^+/p^{\Delta S-U}$ pups, produce long-lasting unsilencing of PWS genes, be well tolerated, and not interfere with the expression of the Angelman syndrome Ube3a gene. Such results achieve a critical step toward the development of a molecularly specific therapy for human PWS. Based on these results, comprehensive evaluation of the efficacy and tolerability of G9a inhibitors in preclinical studies is warranted to fully explore therapeutic potential of G9a inhibitors for treating PWS.

Any patents or publications mentioned in this specification are indicative of the levels of those skilled in the art to which the invention pertains.

One of skill in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of activating at least one maternal copy of candidate Prader-Willi syndrome (PWS) associated genes in a subject in need thereof, the method comprising administering to the subject a G9a inhibitor of Formula I:

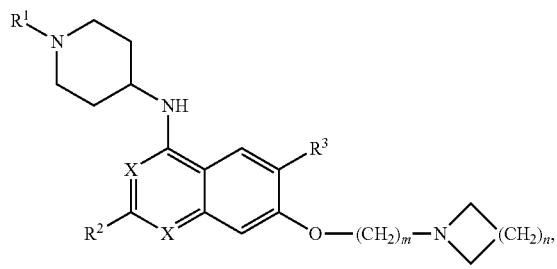

Formula I wherein
- $R^1$ is —$C_1$-$C_8$ alkyl, —$C_3$-$C_8$ cycloalkyl, or —$C_3$-$C_8$heterocycle comprising 1-3 heteroatoms, each of which may be optionally substituted with one or more halogens; each X is independently —CH— or —N—;
- $R^2$ is —$C_3$-$C_8$ cycloalkyl or —$C_3$-$C_8$heterocycle comprising 1-3 heteroatoms, each of which may be optionally substituted with one or more alkyl groups, with one or more halogens, or with a combination thereof;
- $R^3$ is —H, —$C_1$-$C_8$ alkyl, halogen, —CN, —$CF_3$, —$NO_2$ or —$OR^5$;
- wherein $R^5$ is —$C_1$-$C_8$ alkyl; and m and n are each independently 1, 2, 3, 4, or 5.

2. The method according to claim 1, wherein the method further comprises inhibiting the methylation of the histone H3 protein.

3. The method according to claim 2, wherein the methylation of the histone H3 protein at lysine 9 is inhibited.

4. The method according to claim 1, wherein the candidate PWS associated genes are located on the 15q11-q13 region between the MAGEL2 and UBE3A genes.

5. The method according to claim 1, wherein the candidate PWS associated genes comprise MAGEL2, NDN, SNRPN and SnoRNAs genes.

6. The method according to claim 5, wherein the SnoRNAs genes comprise SNORD116 and SNORD115.

7. The method according to claim 1, wherein the G9a inhibitor is

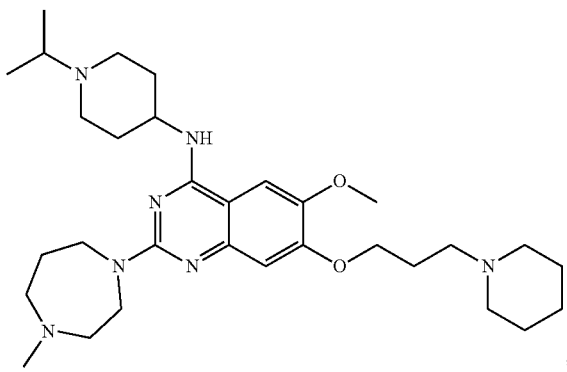
(UNC617)

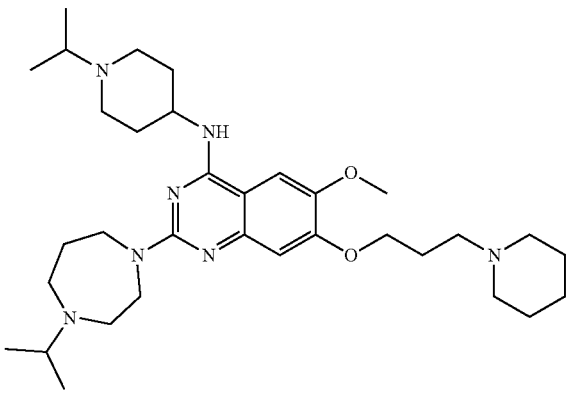
(UNC618)

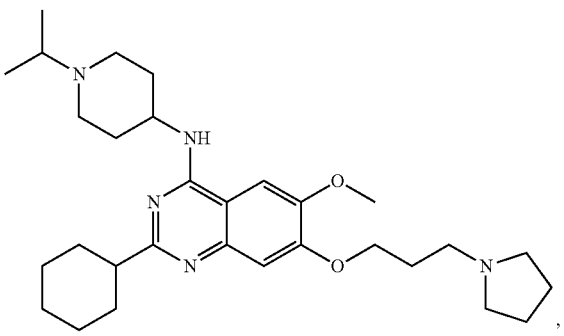
(UNC0638)

(UNC0642)

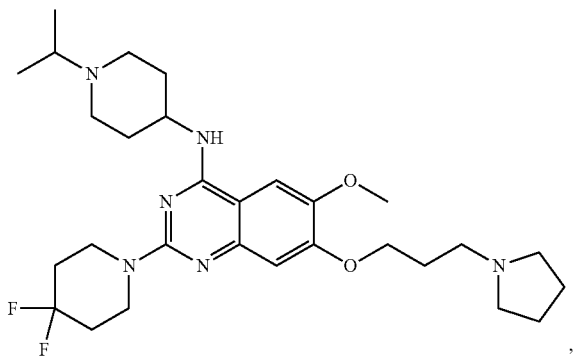

(UNC617)

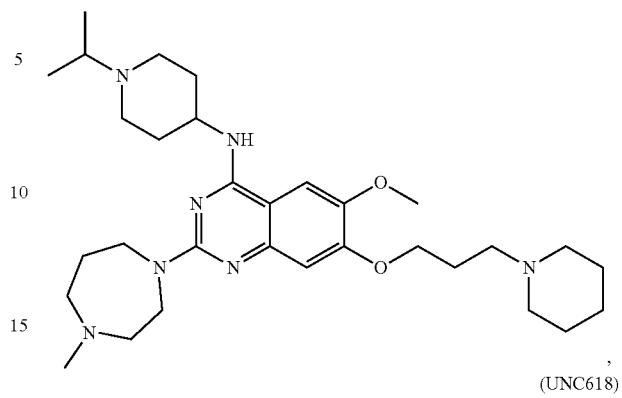

, or any combination thereof.

8. The method according to claim 1, wherein the subject is a human.

9. The method according to claim 1, wherein the method further comprises inhibiting DNA methylation of the PWS associated genes.

10. A method of treating Prader-Willi syndrome (PWS) in a subject in need thereof, the method comprising unsilencing candidate PWS associated genes on the maternal chromosome by administering to the subject a therapeutically effective amount of a G9a inhibitor of Formula I:

Formula I

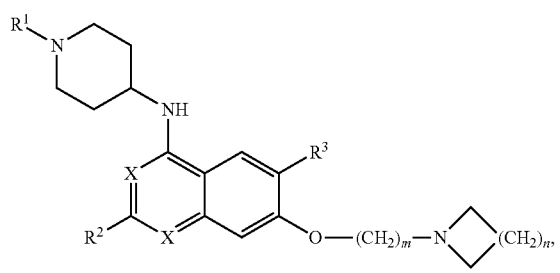

wherein

R$^1$ is —C$_1$-C$_8$ alkyl, —C$_3$-C$_8$ cycloalkyl, or —C$_3$-C$_8$ heterocycle comprising 1-3 heteroatoms, each of which may be optionally substituted with one or more halogens; each X is independently —CH— or —N—;

R$^2$ is —C$_3$-C$_8$ cycloalkyl or —C$_3$-C$_8$ heterocycle comprising 1-3 heteroatoms, each of which may be optionally substituted with one or more alkyl groups, with one or more halogens, or with a combination thereof;

R$^3$ is —H, —C$_1$-C$_8$ alkyl, halogen, —CN, —CF$_3$, —NO$_2$ or —OR$^5$;

wherein R$^5$ is —C$_1$-C$_8$ alkyl; and m and n are each independently 1, 2, 3, 4, or 5.

11. The method of claim 10, wherein the G9a inhibitor reduces the methylation of H3K9.

12. The method according to claim 10, wherein the G9a inhibitor is (UNC618)

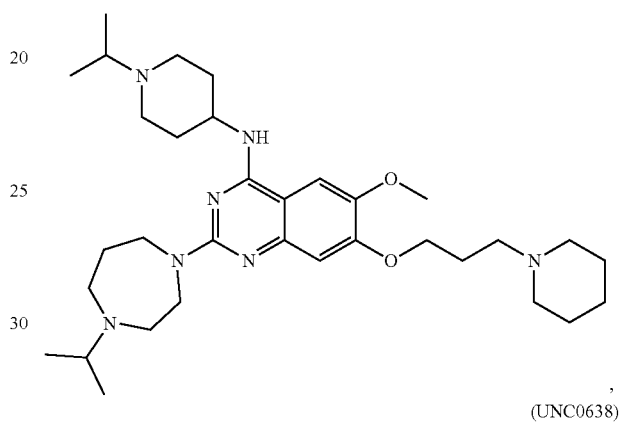

, (UNC0638)

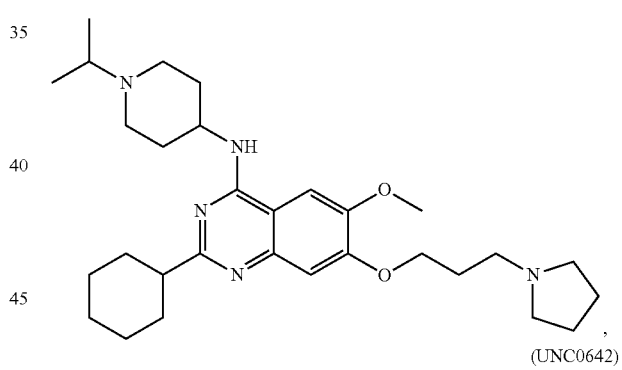

, (UNC0642)

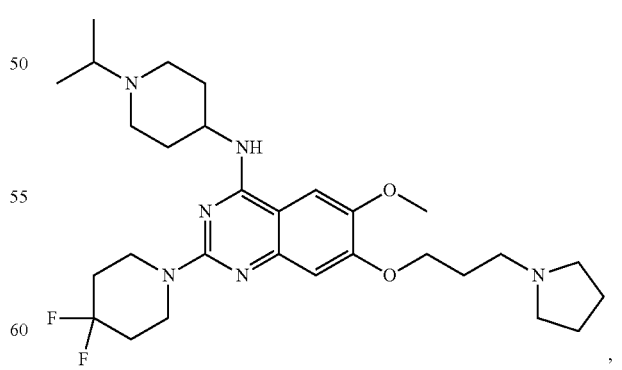

, or any combination thereof.

13. The method according to claim 10, wherein the G9a inhibitor activates at least one gene within the PWS critical region or the PWS-IC-controlled region.

14. The method of claim 13, wherein the at least one gene within the PWS critical region is SNORD116.

15. The method according to claim 10, wherein the subject is a mammal.

16. The method according to claim 15, wherein the subject is a human.

* * * * *